(12) United States Patent
Harris et al.

(10) Patent No.: US 8,435,994 B2
(45) Date of Patent: May 7, 2013

(54) SUBSTITUTED [1,2,4]TRIAZOLO[4,3-ALPHA] QUINOXALINES AS ADENOSINE A2A RECEPTOR ANTAGONISTS

(75) Inventors: Joel M. Harris, Blaine, MN (US); Bernard R. Neustadt, West Orange, NJ (US); Andrew W. Stamford, Chatham, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/510,094

(22) PCT Filed: Nov. 12, 2010

(86) PCT No.: PCT/US2010/056432
§ 371 (c)(1),
(2), (4) Date: May 16, 2012

(87) PCT Pub. No.: WO2011/060207
PCT Pub. Date: May 19, 2011

(65) Prior Publication Data
US 2012/0232086 A1 Sep. 13, 2012

Related U.S. Application Data

(60) Provisional application No. 61/261,538, filed on Nov. 16, 2009.

(51) Int. Cl.
*A61K 31/495* (2006.01)
(52) U.S. Cl.
USPC .............................. 514/250; 544/115; 544/346

(58) Field of Classification Search .................. 514/250; 544/115, 346
See application file for complete search history.

(56) References Cited

U.S. PATENT DOCUMENTS
2008/0255156 A1  10/2008  Clasby et al.

OTHER PUBLICATIONS

Jaakola et al. "The 2.6 Angstrom Crystal Structure of a Human A2a Adenosine Receptor Bound to an Antagonist", Science, vol. 322, 2008, pp. 1211-1217.

*Primary Examiner* — Douglas M Willis
(74) *Attorney, Agent, or Firm* — Gerard M. Devlin; H. Eric Fischer

(57) ABSTRACT

The present invention relates to certain fused tricyclic heteroaryl rings compounds of the Formula (I) (also referred to herein as the "Fused Tricyclic Compounds"), wherein M, Q, U, W, X, Y, Z, $R^1$, $R^2$, and $R^3$, and rings C and D are as herein described. The present invention also provides compositions comprising at least one Fused Tricyclic Compound, and use of such compounds in the treatment of central nervous system diseases or disorders such as Parkinson's disease.

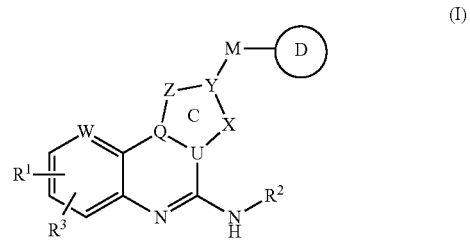

(I)

2 Claims, No Drawings

SUBSTITUTED [1,2,4]TRIAZOLO[4,3-ALPHA] QUINOXALINES AS ADENOSINE A2A RECEPTOR ANTAGONISTS

CROSS REFERENCE TO RELATED APPLICATIONS

This application is the National Stage of International Application No. PCT/US2010/056432 filed on Nov. 12, 2010, which claims the benefit under 35 U.S.C. 119(e) of U.S. Provisional Application No. 61/261,538 filed Nov. 16, 2009, each of which applications are incorporated by reference as if fully set forth herein.

FIELD OF THE INVENTION

The present invention relates to certain fused tricyclic heteroaryl rings compounds of the Formula (I) (also referred to herein as the "Fused Tricyclic Compounds"), compositions comprising at least one Fused Tricyclic Compound, and use of such compounds in the treatment of central nervous system diseases or disorders such as Parkinson's disease.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by its interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_b$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side effects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Adenosine $A_{2a}$ receptor antagonists have been disclosed as being useful in the treatment or prevention of Extra Pyramidal Syndrome (EPS), dystonia, restless leg syndrome (RLS) or periodic limb movement in sleep (PLMS) in International Publication No. WO 2005/044245, and have been disclosed as being useful in the treatment of attention deficit hyperactivity disorder (ADHD) in International Publication No. WO 2002/055083.

SUMMARY OF THE INVENTION

In one aspect, the present invention provides compounds of Formula (I) (herein referred to as the "Fused Tricyclic Compounds"):

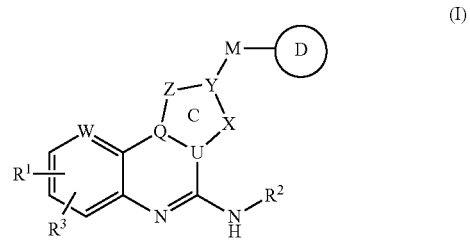

(I)

wherein
W is C($R^4$), or N;
Q is C or N;
U is C or N;
X is C(H) or N;
Y is C or N;
Z is C(H),C=Z', or N;
Z is O, NH, or N—CN;
wherein ring C comprises Q, U, X, Y, and Z, and is selected from one of the following rings:

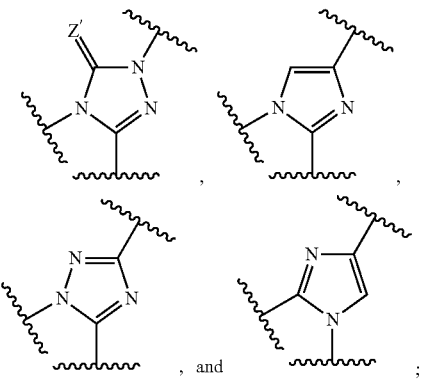

M is a direct bond, C=O, ($C_1$-$C_4$)alkylene, or ($C_1$-$C_4$) alkylene substituted by ($C_1$-$C_3$)alkyl or hydroxy;

D is phenyl or 3 to 7-membered ring cycloalkyl, wherein said phenyl or cycloalkyl of D is unsubstituted or substituted by one to three moieties independently selected from the group consisting of ($C_1$-$C_6$)alkyl, hydroxy ($C_1$-$C_6$)alkyl; ($C_1$-$C_6$)alkoxy, halo, trifluoromethyl, cyano, nitro, amino, ($C_1$-$C_6$)alkylamino, di-($C_1$-$C_6$)alkylamino, di-($C_1$-$C_6$)alkylaminomethinylamino, ($C_1$-$C_6$)alkanoylamino, ($C_1$-$C_6$) alkoxycarbonyl, di-($C_1$-$C_6$)alkylcarbamoyl, morpholinocarbonyl, and ($C_1$-$C_6$)alkylsulfonyl;

$R^1$ and $R^3$ are independently selected from the group consisting of H, ($C_1$-$C_6$)alkyl, hydroxy ($C_1$-$C_6$)alkyl; ($C_1$-$C_6$) alkoxy, halo, trifluoromethyl, cyano, nitro, amino, ($C_1$-$C_6$) alkylamino, di-($C_1$-$C_6$)alkylamino, ($C_1$-$C_6$)alkanoyl, ($C_1$-$C_6$)alkanoylamino, and ($C_1$-$C_6$)alkoxycarbonyl;

$R^2$ is selected from the group consisting of H and ($C_1$-$C_6$) alkyl;

$R^4$ is selected from the group consisting of H and ($C_1$-$C_6$) alkyl; and with the proviso that when ring C is

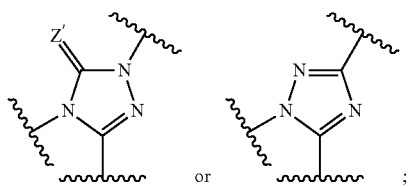

then M is $(C_1-C_4)$alkylene or $(C_1-C_4)$alkylene substituted by $(C_1-C_3)$alkyl or hydroxy; or a pharmaceutically acceptable salt thereof.

The invention also provides a pharmaceutical composition comprising a therapeutically effective amount of a Fused Tricyclic Compound or a pharmaceutically acceptable salt thereof, and a pharmaceutically acceptable carrier.

The invention also provides a method for treating Parkinson's disease, depression, extra-pyramidal syndrome, an attention deficit disorder, or restless leg syndrome, comprising administering a therapeutically effective amount of a Fused Tricyclic Compound, or a pharmaceutically acceptable salt thereof to a patient in need of such treatment. In some embodiments, the method further comprises administering dopaminergic agent to the patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

The present invention provides Fused Tricyclic Compounds, pharmaceutical compositions comprising at least one Fused Tricyclic Compound, and methods of using the Fused Tricyclic Compounds for treating various central nervous system diseases or disorders such as Parkinson's disease in a patient, e.g., a human patient.

Definitions and Abbreviations

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The "alkynyl" may be unsubstituted or optionally substituted by one or more substituents which may be the same or different, each substituent being independently selected from the group consisting of aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, (uranyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which ring system contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. A non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred halogens are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., —NY$_1$Y$_2$, -alkyl-NY$_1$Y$_2$, —C(O)NY$_1$Y$_2$, —SO$_2$NY$_1$Y$_2$ and —S(O)NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such a moiety are methylene dioxy, ethylenedioxy, —C(CH$_3$)$_2$— and the like which form moieties such as, for example:

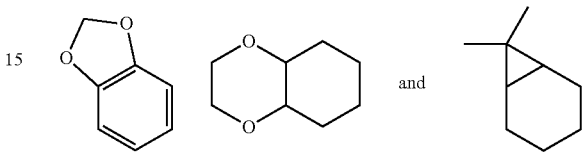

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example, nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom, respectively, is present as a ring atom. Any —NH in a heterocyclyl ring may exist in protected form such as, for example, as an —N(Boc), —N(Cbz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is

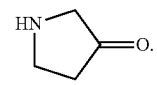

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thin before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

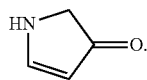

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

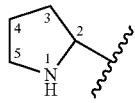

there is no —OH attached directly to carbons marked 2 and 5.

It should also be noted that tautomeric forms such as, for example, the moieties:

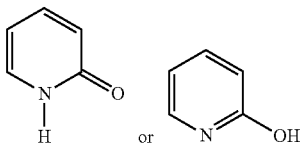

are considered equivalent in certain embodiments of this invention.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. A non-limiting example of a suitable aralkylthio group is benzylthio. The bond to the parent moiety is through the sulfur.

"Alkoxycarbonyl" means an alkyl-O—C(O)— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. A reference to a "stable compound" or "stable structure" means that the compound is sufficiently robust to survive isolation to a useful degree of purity from a reaction mixture, and to survive formulation into an efficacious therapeutic agent.

The term "optionally substituted" means optional substitution with the specified groups, radicals or moieties.

Lines drawn into the ring systems, such as, for example:

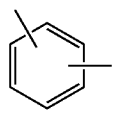

indicate that the indicated line (bond) may be attached to any of the substitutable ring carbon atoms.

The term "purified", "in purified form" or "in isolated and purified form" for a compound refers to the physical state of said compound after being isolated from a synthetic process (e.g., from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. In addition, any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino $(C_1-C_4)$alkyl or mono-N or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I) can form salts which are also within the scope of this invention. Reference to a compound of Formula (I) or a Fused Tricyclic Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

The compounds of Formula (I), and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. For instance those compounds labeled with positron-emitting isotopes like $^{11}C$ or $^{18}F$ can be useful for application in Positron Emission Tomography (PET) and those labeled with gamma ray emitting isotopes like $^{123}I$ can be useful for application in Single Photon Emission Computed Tomography (SPECT). Further, substitution of compounds with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution of a compound at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula (I), and of the salts, solvates, esters and prodrugs of the compounds of Formula (I), are intended to be included in the present invention.

The present invention further includes the compounds of Formula (I) in all their isolated forms. For example, the above-identified compounds are intended to encompass all forms of the compounds such as, any solvates, hydrates, stereoisomers, and tautomers thereof.

The compounds according to the invention have pharmacological properties; in particular, the compounds of Formula (I) can be antagonists of the adenosine $A_{2a}$ receptor.

The following abbreviations are used below and have the following meanings: Me is methyl; Bu is butyl; Et is ethyl; BINAP is racemic-2,2'-bis(diphenylphosphino)-1,1'-binaphthyl; BOC or Boc is tert-butyloxycarbonyl; CDI is carbonyl diimidazole; Ci/mmol is Curie/mmol; CSA is camphorsulfonic acid; DBPD is 2-(Di-t-butylphosphino)biphenyl, DBU is 1,8-diazabicyclo[5.4.0]undec-7-ene; DBN is 1,5-diazabicyclo[4.3.0]non-5-ene; DCC is dicyclohexylcarbodiimide; DCM is dichloromethane; Dibal-His diisobutylaluminum hydride; DIPEA is N,N-Diisopropylethylamine; DMAP is dimethylaminopyridine; DME is dimethoxyethane; DMF is dimethylformamide; dppf is diphenylphosphinoferrocene; EDCI is 1-(3-dimethylaminopropyl)-3-ethylcarbodiimide; EtOAc is ethyl acetate; FABMS is fast atom bombardment mass spectrometry; HATU is O-(7-azabenzotriazol-1-yl)-N,N,N',N'-tetramethyluronium hexafluorophosphate; HOBT is 1-hydroxybenzotriazole; HOOBt is 3-hydroxy-1,2,3-benzotriazin-4(3H)-one; HPLC is high performance liquid chromatography; HRMS is high resolution mass spectrometry; Hunig's base is N,N-diisopropylethylamine; LAH is lithium aluminum hydride; LDA is lithium diisopropylamide; LRMS is low resolution mass spectrometry; m-CPBA is m-chloroperbenzoic acid; MeOH is methanol; $NaBH(OAc)_3$ is sodium triacetoxyborohydride; NaHMDS is sodium hexamethyldisilazane; $NH_4OAc$ is ammonium acetate; p-TsOH is p-toluenesulfonic acid; p-TsCl is p-toluenesulfonyl chloride; PLC is preparative layer chromatography; PPTS is pyridinium p-toluenesulfonate; PYBROP is bromotripyrrolidinophosphonium hexafluorophosphate; RT is room temperature; SEM is β-(trimethylsilyl)ethoxy]methyl; SEMCl is β-(trimethylsilyl)ethoxy]methyl chloride; TFA is trifluoroacetic acid; THF is tetrahydrofuran; TLC is thin-layer chromatography; TMAD is N,N,N',N'-tetramethylazodicarboxamide; Tr is triphenylmethyl; and Tris is tris(hydroxymethyl)aminomethane.

The Compounds of Formula (I)

In one aspect, the present invention provides compounds of Formula (I):

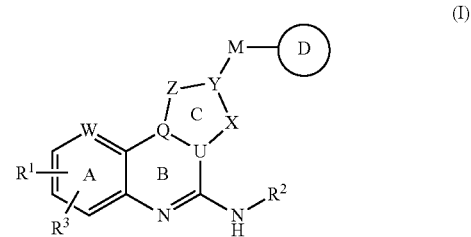

or pharmaceutically acceptable salts thereof, wherein M, Q, U, W, X, Y, Z, $R^2$, and $R^3$, and rings C and D are as described above for the compounds of Formula (I).

As used herein, including the claims, when referring to specific embodiments of ring C, the designation of ring C as:

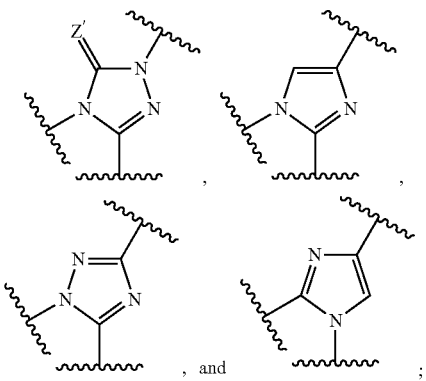

is intended to mean that the left and bottom truncated bonds extending from ring C form part of the central ring or B ring of the compound of Formula (I) and the right truncated bond extending from ring C joins the M moiety.

In specific embodiments, the compounds of Formula (I) are in the form of pharmaceutically acceptable salts.

In certain embodiments, the compounds of Formula (I) are in purified form.

In some embodiments of the compounds of Formula (I), W is $C(R^4)$.

In certain embodiments of the compounds of Formula (I), M is C=O or $(C_1-C_4)$alkylene.

In some embodiments of the compounds of Formula (I), M is $(C_1-C_4)$alkylene substituted by $(C_1-C_3)$alkyl or hydroxy.

In specific embodiments of the compounds of Formula (I), M is methylene.

In some embodiments of the compounds of Formula (I), D is unsubstituted cycloalkyl, unsubstituted phenyl, or phenyl substituted by one to three moieties independently selected from the group consisting of $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, di-$(C_1-C_6)$alkylaminomethinylamino, $(C_1-C_6)$alkanoylamino, $(C_1-C_6)$alkoxycarbonyl, di-$(C_1-C_6)$alkylcarbamoyl, morpholinocarbonyl, and $(C_1-C_6)$alkylsulfonyl.

In certain embodiments of the compounds of Formula (I), $R^1$ and $R^3$ are not substituted on the top (northern-most) atom of ring A of the tricyclic core structure.

In specific embodiments, the compounds of the Formula (IA) are selected from compounds 1-62 whose structures are set forth below.

In another aspect, the compounds of the Formula (I) have the Formula (IA):

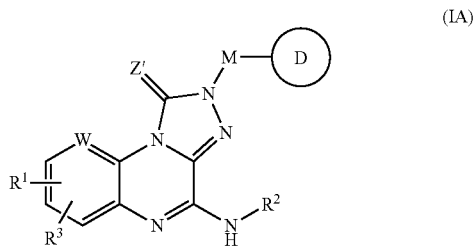

(IA)

wherein

W is $C(R^4)$, or N;

Z' is O, NH, or N—CN;

M is $(C_1-C_4)$alkylene or $(C_1-C_4)$alkylene substituted by $(C_1-C_3)$alkyl;

D is phenyl or 3 to 7-membered ring cycloalkyl, wherein said phenyl or cycloalkyl of D is unsubstituted or substituted by one to three moieties independently selected from the group consisting of $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, di-$(C_1-C_6)$alkylaminomethinylamino, $(C_1-C_6)$alkanoylamino, $(C_1-C_6)$alkoxycarbonyl, di-$(C_1-C_6)$alkylcarbamoyl, morpholinocarbonyl, and $(C_1-C_6)$alkylsulfonyl;

$R^1$ and $R^3$ are independently selected from the group consisting of H, $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, $(C_1-C_6)$alkanoyl, $(C_1-C_6)$alkanoylamino, and $(C_1-C_6)$alkoxycarbonyl;

$R^2$ is selected from the group consisting of H and $(C_1-C_6)$alkyl; and $R^4$ is selected from the group consisting of H and $(C_1-C_6)$alkyl.

In some embodiments of the compounds of the Formula (IA), W is C(H).

In certain embodiments of the compounds of the Formula (IA), Z' is O.

In other embodiments of the compounds of the Formula (IA), Z' is NH or N—C≡N.

In some embodiments of the compounds of the Formula (IA), M is $(C_1-C_4)$alkylene.

In specific embodiments of the compounds of the Formula (IA), M is methylene.

In certain embodiments of the compounds of the Formula (IA), D is unsubstituted cyclopropyl.

In other embodiments of the compounds of the Formula (IA), D is unsubstituted cyclopropyl, unsubstituted phenyl, or phenyl substituted by one to three moieties independently selected from the group consisting of $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, di-$(C_1-C_6)$alkylaminomethinylamino, $(C_1-C_6)$alkanoylamino, $(C_1-C_6)$alkoxycarbonyl, di-$(C_1-C_6)$alkylcarbamoyl, morpholinocarbonyl, and $(C_1-C_6)$alkylsulfonyl.

In other embodiments of the compounds of the Formula (IA), D is unsubstituted phenyl, or phenyl substituted by one to three moieties independently selected from the group consisting of $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, di-$(C_1-C_6)$alkylaminomethinylamino, $(C_1-C_6)$alkanoylamino, $(C_1-C_6)$alkoxycarbonyl, di-$(C_1-C_6)$alkylcarbamoyl, morpholinocarbonyl, and $(C_1-C_6)$alkylsulfonyl.

In other embodiments of the compounds of the Formula (IA), W is C(H); Z' is O; M is $(C_1-C_4)$alkylene; and D is unsubstituted cyclopropyl, unsubstituted phenyl, or phenyl substituted by one to three moieties independently selected from the group consisting of $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, di-$(C_1-C_6)$alkylaminomethinylamino, $(C_1-C_6)$alkanoylamino, $(C_1-C_6)$alkoxycarbonyl, di-$(C_1-C_6)$alkylcarbamoyl, morpholinocarbonyl, and $(C_1-C_6)$alkylsulfonyl.

In specific embodiments the compounds of the Formula (IA) are selected from the compounds presented in Table I, below. In addition to identifying the compound, each entry in Table I identifies the activity of that compound by reporting a Ki value (in nM) in the column adjacent to the structural representation of the compound. Ki values reported in Table I for each compound were determined by the assay described in Example 25, herein below. Selected entries in Table I relate also the mass data for the compound, as determined by mass spectroscopy described in the Examples, below.

TABLE I

| Example No. | Structure | Activity (Ki, nM) | M/e |
|---|---|---|---|
| 1 | 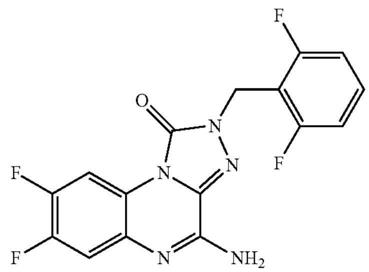 [SMILES: Nc1nc2cc(F)c(F)cc2n2c(=O)n(Cc3c(F)cccc3F)nc12] | 0.4 | 364 |
| 2 | 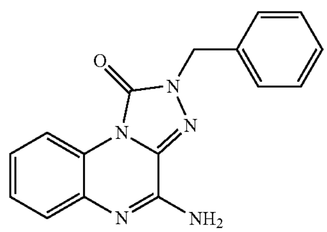 [SMILES: Nc1nc2ccccc2n2c(=O)n(Cc3ccccc3)nc12] | 0.7 | 292.2 |
| 3 | 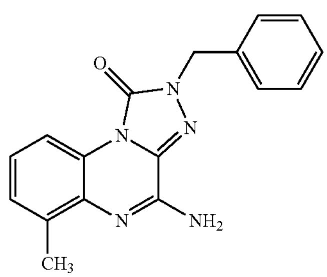 [SMILES: Cc1cccc2c1nc(N)c1nn(Cc3ccccc3)c(=O)n12] | 0.6 | 306 |
| 4 | 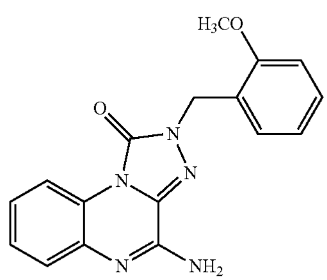 [SMILES: COc1ccccc1Cn1nc2c(N)nc3ccccc3n2c1=O] | 0.7 | 299.2 |
| 5 | 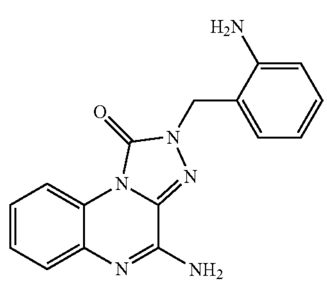 [SMILES: Nc1ccccc1Cn1nc2c(N)nc3ccccc3n2c1=O] | 0.7 | |
| 6 | 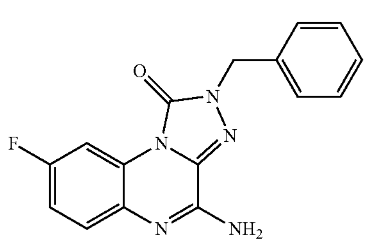 [SMILES: Nc1nc2ccc(F)cc2n2c(=O)n(Cc3ccccc3)nc12] | 0.9 | 310.2 |

TABLE I-continued
| Example No. | Structure | Activity (Ki, nM) | M/e |
|---|---|---|---|
| 7 | 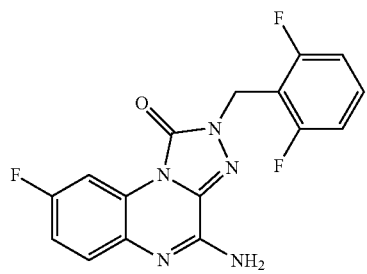 [SMILES: Nc1nc2ccc(F)cc2n2c(=O)n(Cc3c(F)cccc3F)nc12] | 0.7 | 346.2 |
| 8 | 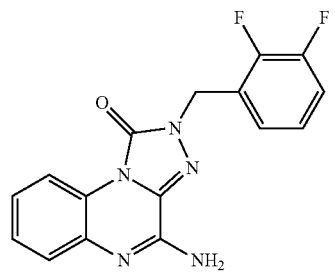 [SMILES: Nc1nc2ccccc2n2c(=O)n(Cc3cccc(F)c3F)nc12] | 1.0 | 328.1 |
| 9 | 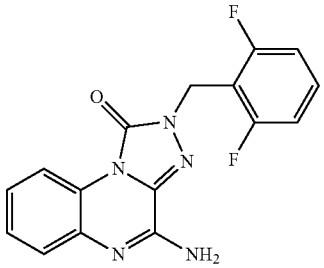 [SMILES: Nc1nc2ccccc2n2c(=O)n(Cc3c(F)cccc3F)nc12] | 1.0 | 328.2 |
| 10 | 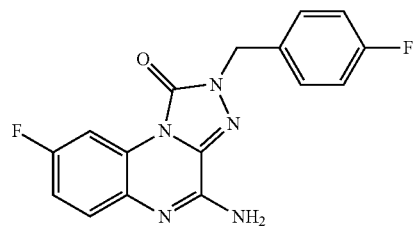 [SMILES: Nc1nc2ccc(F)cc2n2c(=O)n(Cc3ccc(F)cc3)nc12] | 1.0 | 328.2 |
| 11 | 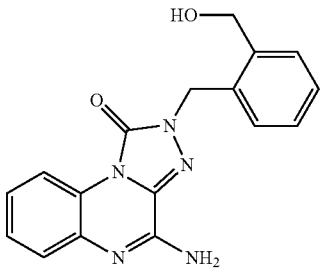 [SMILES: Nc1nc2ccccc2n2c(=O)n(Cc3ccccc3CO)nc12] | 1.2 | |

TABLE I-continued

| Example No. | Structure | Activity (Ki, nM) | M/e |
|---|---|---|---|
| 12 | 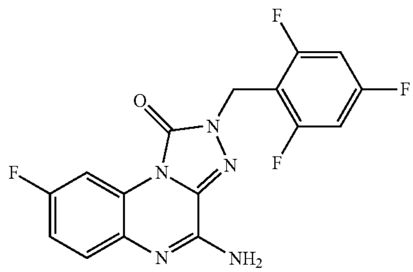 [SMILES: Nc1nc2ccc(F)cc2n2c(=O)n(Cc3c(F)cc(F)cc3F)nc12] | 1.0 | 364.2 |
| 13 | 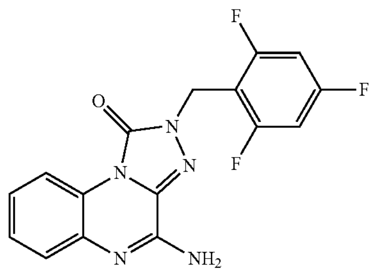 [SMILES: Nc1nc2ccccc2n2c(=O)n(Cc3c(F)cc(F)cc3F)nc12] | 1.4 | 346.2 |
| 14 | 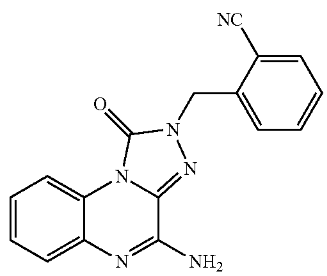 [SMILES: N#Cc1ccccc1Cn1nc2c(N)nc3ccccc3n2c1=O] | 1.2 | 317.2 |
| 15 | 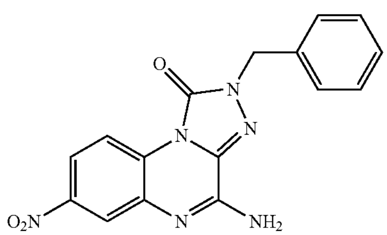 [SMILES: Nc1nc2cc([N+](=O)[O-])ccc2n2c(=O)n(Cc3ccccc3)nc12] | 1.4 | 337 |
| 16 | 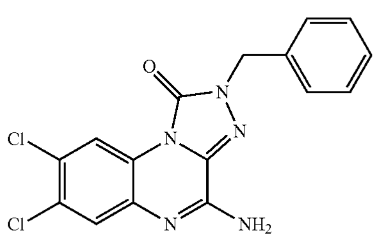 [SMILES: Nc1nc2cc(Cl)c(Cl)cc2n2c(=O)n(Cc3ccccc3)nc12] | 1.4 | |
| 17 | 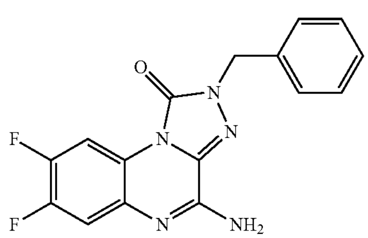 | 1.4 | 328 |

TABLE I-continued

| Example No. | Structure | Activity (Ki, nM) | M/e |
|---|---|---|---|
| 18 | (4-fluorobenzyl derivative) | 1.9 | 310.2 |
| 19 | (benzyl, H₃CO₂C-substituted derivative) | 1.7 | 350 |
| 20 | (2,6-difluorobenzyl, F₃C-substituted derivative) | 1.8 | 396 |
| 21 | (2-trifluoromethylbenzyl derivative) | 1.8 | 360 |
| 22 | (2-fluoro-6-trifluoromethylbenzyl, F-substituted derivative) | 2.2 | 396.2 |

TABLE I-continued

| Example No. | Structure | Activity (Ki, nM) | M/e |
|---|---|---|---|
| 23 | (structure) | 2.0 | |
| 24 | (structure) | 2.8 | 382 |
| 25 | (structure) | 2.6 | |
| 26 | (structure) | 1.9 | 350 |
| 27 | (structure) | 2.5 | 378.2 |

TABLE I-continued

| Example No. | Structure | Activity (Ki, nM) | M/e |
|---|---|---|---|
| 28 | 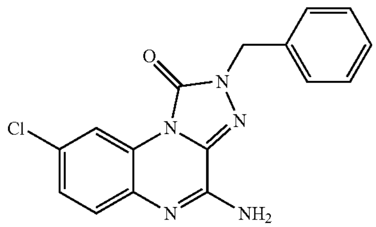 [SMILES: Nc1nc2ccc(Cl)cc2n2c(=O)n(Cc3ccccc3)nc12] | 2.7 | 326.2 |
| 29 | 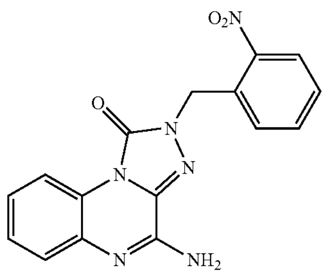 [SMILES: Nc1nc2ccccc2n2c(=O)n(Cc3ccccc3[N+](=O)[O-])nc12] | 3.2 | 337 |
| 30 | 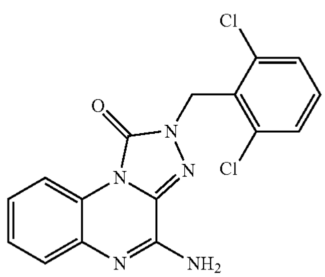 [SMILES: Nc1nc2ccccc2n2c(=O)n(Cc3c(Cl)cccc3Cl)nc12] | 3.2 | 360.2 |
| 31 | 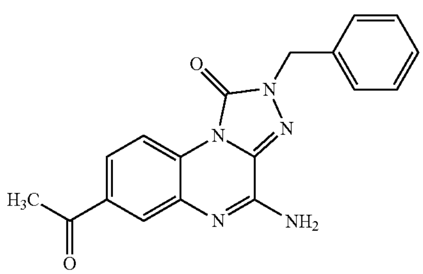 [SMILES: CC(=O)c1ccc2c(c1)nc(N)c1nn(Cc3ccccc3)c(=O)n12] | 3.0 | |
| 32 | 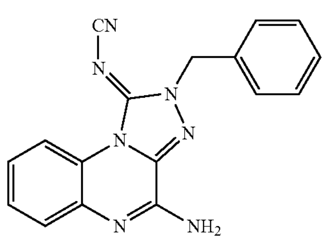 [SMILES: N#C/N=c1\n(Cc2ccccc2)nc2c(N)nc3ccccc3n12] | 4.7 | |
| 33 | 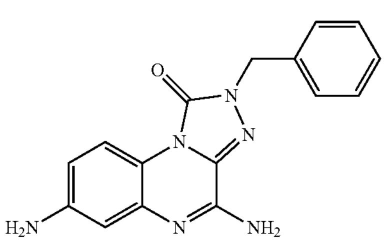 | 5.6 | |

TABLE I-continued

| Example No. | Structure | Activity (Ki, nM) | M/e |
|---|---|---|---|
| 34 | 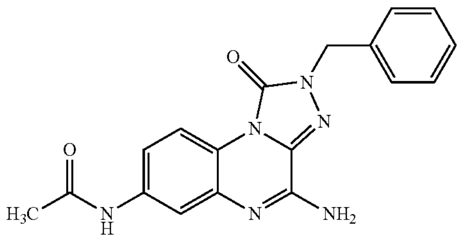 [SMILES: CC(=O)Nc1ccc2c(c1)nc(N)c1nn(Cc3ccccc3)c(=O)n12] | 99.3 | |
| 35 | 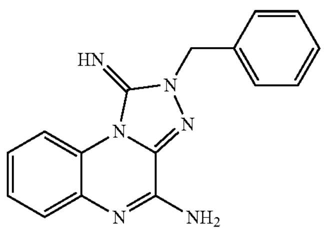 [SMILES: N=c1n(Cc2ccccc2)nc2c(N)nc3ccccc3n12] | 6.0 | |
| 36 | 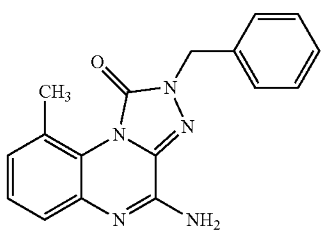 [SMILES: Cc1cccc2nc(N)c3nn(Cc4ccccc4)c(=O)n3c12] | 7.1 | |
| 37 | 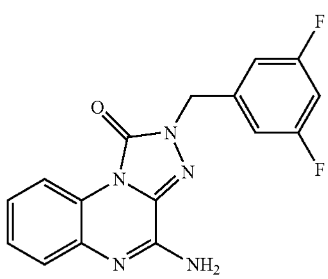 [SMILES: Nc1nc2ccccc2n2c(=O)n(Cc3cc(F)cc(F)c3)nc12] | 7.4 | |
| 38 | 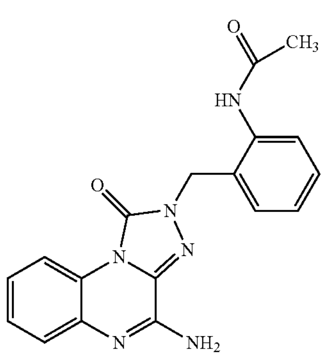 [SMILES: CC(=O)Nc1ccccc1Cn1nc2c(N)nc3ccccc3n2c1=O] | 7.4 | |

TABLE I-continued
| Example No. | Structure | Activity (Ki, nM) | M/e |
|---|---|---|---|
| 39 | 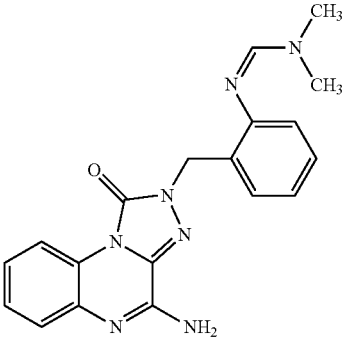 [SMILES: CN(C)/C=N\c1ccccc1Cn1nc2c(N)nc3ccccc3n2c1=O] | 8.2 | |
| 40 | 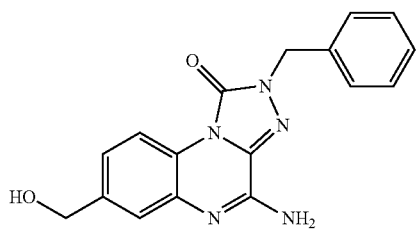 [SMILES: Nc1nc2cc(CO)ccc2n2c(=O)n(Cc3ccccc3)nc12] | 8.6 | |
| 41 | 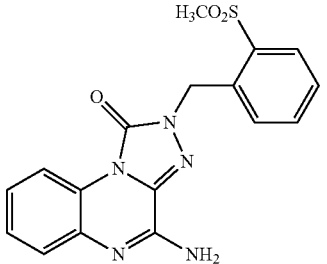 | 8.3 | 370.2 |
| 42 | 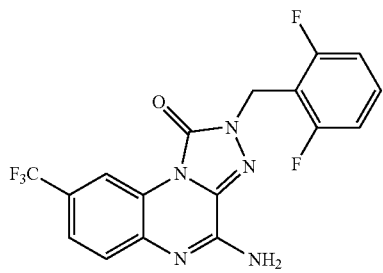 [SMILES: Nc1nc2ccc(C(F)(F)F)cc2n2c(=O)n(Cc3c(F)cccc3F)nc12] | 10.2 | 396 |
| 43 | 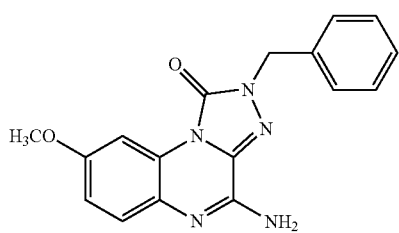 [SMILES: COc1ccc2nc(N)c3nn(Cc4ccccc4)c(=O)n3c2c1] | 12.1 | 322.2 |

TABLE I-continued

| Example No. | Structure | Activity (Ki, nM) | M/e |
|---|---|---|---|
| 44 | 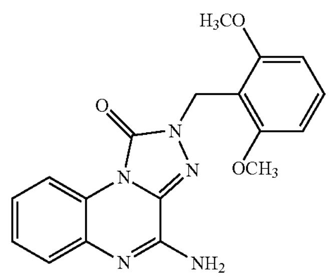 [SMILES: COc1cccc(OC)c1Cn1nc2c(N)nc3ccccc3n2c1=O] | 14.0 | 352.2 |
| 45 | 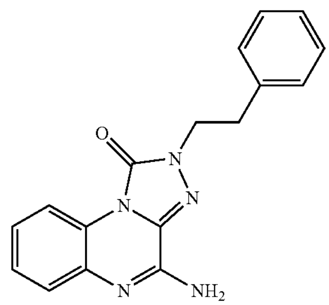 [SMILES: Nc1nc2ccccc2n2c(=O)n(CCc3ccccc3)nc12] | 29.2 | 306.1 |
| 46 | 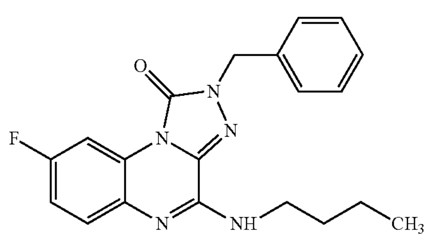 [SMILES: CCCCNc1nc2ccc(F)cc2n2c(=O)n(Cc3ccccc3)nc12] | 28.9 | |
| 47 | 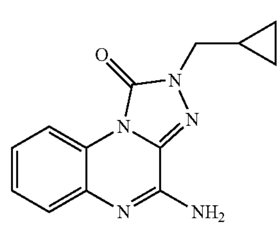 [SMILES: Nc1nc2ccccc2n2c(=O)n(CC3CC3)nc12] | 32.3 | 256.1 |
| 48 | 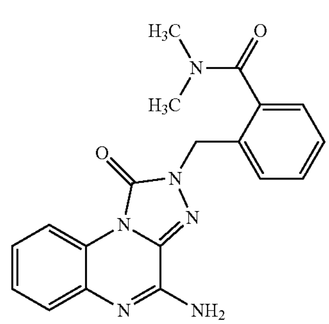 [SMILES: CN(C)C(=O)c1ccccc1Cn1nc2c(N)nc3ccccc3n2c1=O] | 28.9 | |

TABLE I-continued

| Example No. | Structure | Activity (Ki, nM) | M/e |
|---|---|---|---|
| 49 | 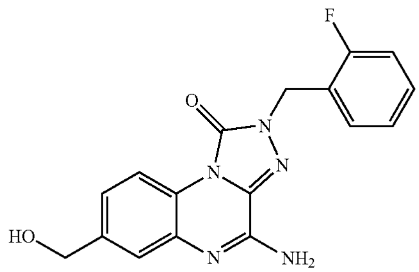 [SMILES: Nc1nc2cc(CO)ccc2n2c(=O)n(Cc3ccccc3F)nc12] | 38.4 | |
| 50 | 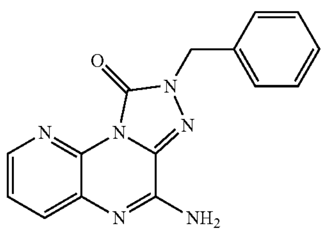 [SMILES: Nc1nc2cccnc2n2c(=O)n(Cc3ccccc3)nc12] | 46.3 | 293.2 |
| 51 | 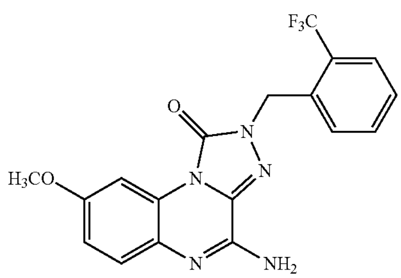 [SMILES: COc1ccc2nc(N)c3nn(Cc4ccccc4C(F)(F)F)c(=O)n3c2c1] | 51.5 | 390.2 |
| 52 | 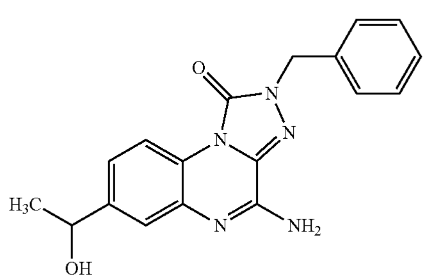 [SMILES: CC(O)c1ccc2c(c1)nc(N)c1nn(Cc3ccccc3)c(=O)n12] | 54.9 | |
| 53 | 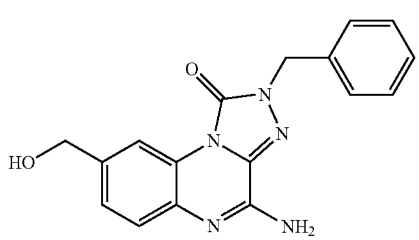 [SMILES: Nc1nc2ccc(CO)cc2n2c(=O)n(Cc3ccccc3)nc12] | 60.0 | |

TABLE I-continued

| Example No. | Structure | Activity (Ki, nM) | M/e |
|---|---|---|---|
| 54 | 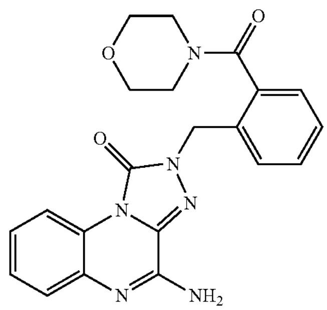 [SMILES: Nc1nc2ccccc2n2c(=O)n(Cc3ccccc3C(=O)N3CCOCC3)nc12] | 66.4 | |
| 55 | 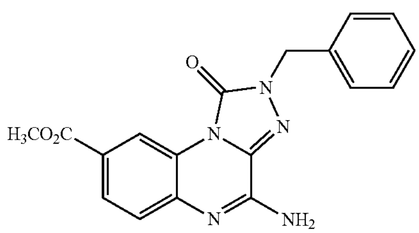 [SMILES: COC(=O)c1ccc2nc(N)c3nn(Cc4ccccc4)c(=O)n3c2c1] | 70.8 | 350 |
| 56 | 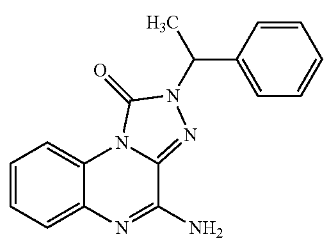 [SMILES: CC(c1ccccc1)n1nc2c(N)nc3ccccc3n2c1=O] | 91.1 | 306.02 |

In another aspect, the compounds of the Formula (I) have the Formula (IB):

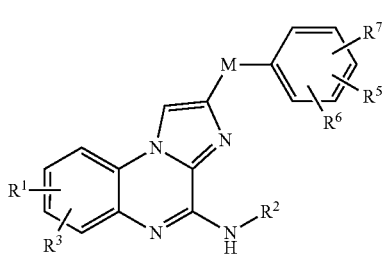

(IB)

wherein

M is a direct bond, C=O, ($C_1$-$C_4$)alkylene, or ($C_1$-$C_4$) alkylene substituted by ($C_1$-$C_3$)alkyl or hydroxy;

$R^1$ and $R^3$ are independently selected from the group consisting of H, ($C_1$-$C_6$)alkyl, hydroxy ($C_1$-$C_6$)alkyl; ($C_1$-$C_6$) alkoxy, halo, trifluoromethyl, cyano, nitro, amino, ($C_1$-$C_6$) alkylamino, di-($C_1$-$C_6$)alkylamino, ($C_1$-$C_6$)alkanoyl, ($C_1$-$C_6$)alkanoylamino, and ($C_1$-$C_6$)alkoxycarbonyl;

$R^2$ is selected from the group consisting of H and ($C_1$-$C_6$) alkyl; and $R^5$, $R^6$, and $R^7$ are independently selected from the group consisting of H, ($C_1$-$C_6$)alkyl, hydroxy ($C_1$-$C_6$)alkyl; ($C_1$-$C_6$) alkoxy, halo, trifluoromethyl, cyano, nitro, amino, ($C_1$-$C_6$) alkylamino, di-($C_1$-$C_6$)alkylamino, di-($C_1$-$C_6$)alkylaminomethinylamino, ($C_1$-$C_6$)alkanoylamino, ($C_1$-$C_6$) alkoxycarbonyl, di-($C_1$-$C_6$)alkylcarbamoyl, morpholinocarbonyl, and ($C_1$-$C_6$)alkylsulfonyl.

In some embodiments of the compounds of the Formula (IB), M is a direct bond (such that the phenyl ring bearing $R^5$, $R^6$, and $R^7$ is attached directly to ring C), C=O, —CH$_2$—, or —CH(OH).

In certain embodiments of the compounds of the Formula (IB), $R^2$ is H.

In specific embodiments of the compounds of the Formula (IB), $R^1$ and $R^3$ are independently H or halo.

In some embodiments of the compounds of the Formula (IB), M is a direct bond, C=O, —CH$_2$—, or —CH(OH); $R^2$ is H; $R^1$ and $R^3$ are independently H or halo; and $R^5$, $R^6$, and $R^7$ are H or halo. In specific instances of such embodiments, R', $R^3$, $R^5$, $R^6$, and $R^7$ are H. In specific embodiments the compounds of the Formula (IB) are selected from the compounds shown in Table II, below. In addition to identifying the compound, each entry in Table II identifies the activity of that compound by reporting a Ki value (in nM) in the column adjacent to the structural representation of the compound. Ki values reported in Table II for each compound were determined by the assay described in Example 25, herein below.

TABLE II

| Exple No. | Structure | Activity (Ki in nM) |
|---|---|---|
| 57 | 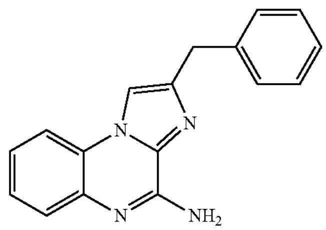 [SMILES: Nc1nc2ccccc2n2cc(Cc3ccccc3)nc12] | 4.1 |
| 58 | 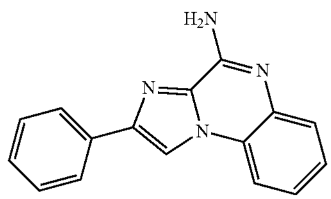 [SMILES: Nc1nc2ccccc2n2cc(-c3ccccc3)nc12] | 57 |
| 59 | 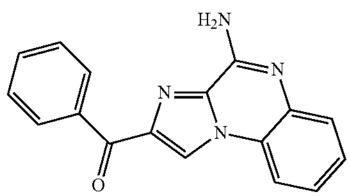 [SMILES: Nc1nc2ccccc2n2cc(C(=O)c3ccccc3)nc12] | 42 |
| 60 | 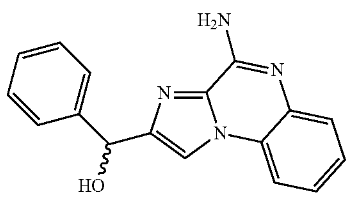 [SMILES: Nc1nc2ccccc2n2cc(C(O)c3ccccc3)nc12] | 29 |

In another aspect, the compounds of the Formula (I) have the Formula (IC):

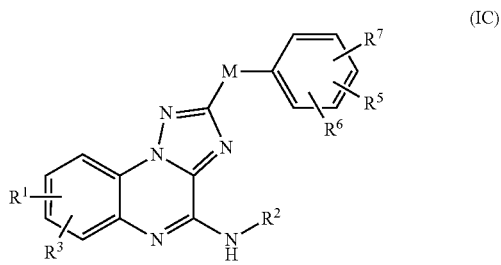

(IC)

wherein

M is $(C_1-C_4)$alkylene or $(C_1-C_4)$alkylene substituted by $(C_1-C_3)$alkyl or hydroxy;

$R^1$ and $R^3$ are independently selected from the group consisting of H, $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, $(C_1-C_6)$alkanoyl, $(C_1-C_6)$alkanoylamino, and $(C_1-C_6)$alkoxycarbonyl;

$R^2$ is selected from the group consisting of H and $(C_1-C_6)$alkyl; and $R^5$, $R^6$, and $R^7$ are independently selected from the group consisting of H, $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, di-$(C_1-C_6)$alkylaminomethinylamino, $(C_1-C_6)$alkanoylamino, $(C_1-C_6)$alkoxycarbonyl, di-$(C_1-C_6)$alkylcarbamoyl, morpholinocarbonyl, and $(C_1-C_6)$alkylsulfonyl.

In some embodiments of the compounds of Formula (IC), M is —$CH_2$—.

In certain embodiments of the compounds of Formula (IC), $R^2$ is H.

In some embodiments of the compounds of Formula (IC), $R^1$ and $R^3$ are independently H or halo.

In certain embodiments of the compounds of Formula (IC), $R^5$, $R^6$, and $R^7$ are independently H or halo.

In specific embodiments of the compounds of Formula (IC), M is —$CH_2$—; $R^2$ is H; $R^1$ and $R^3$ are independently H or halo; and $R^5$, $R^6$, and $R^7$ are independently H or halo. In specific instances of such embodiments, $R^1$, $R^3$, $R^5$, $R^6$, and $R^7$ are H.

In a specific embodiment, the compound of the Formula (IC) is the compound of Formula 61, which has been found to have activity yielding a Ki value of 0.7 nM as determined by the assay described in Example 25, below.

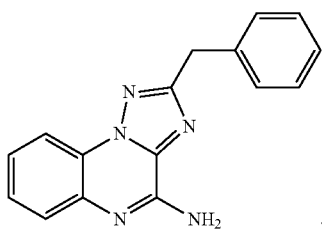

61

In another aspect, the compounds of the Formula (I) have the Formula (ID):

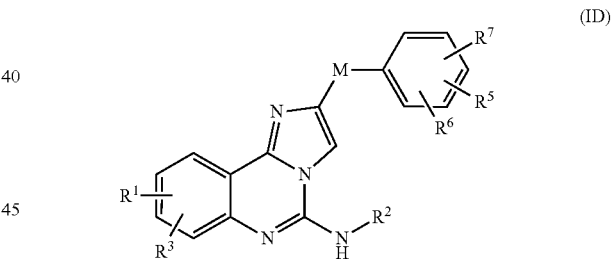

(ID)

wherein

M is $(C_1-C_4)$alkylene or $(C_1-C_4)$alkylene substituted by $(C_1-C_3)$alkyl or hydroxy;

$R^1$ and $R^3$ are independently selected from the group consisting of H, $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, $(C_1-C_6)$alkanoyl, $(C_1-C_6)$alkanoylamino, and $(C_1-C_6)$alkoxycarbonyl;

$R^2$ is selected from the group consisting of H and $(C_1-C_6)$alkyl; and $R^5$, $R^6$, and $R^7$ are independently selected from the group consisting of H, $(C_1-C_6)$alkyl, hydroxy $(C_1-C_6)$alkyl; $(C_1-C_6)$alkoxy, halo, trifluoromethyl, cyano, nitro, amino, $(C_1-C_6)$alkylamino, di-$(C_1-C_6)$alkylamino, di-$(C_1-C_6)$alkylaminomethinylamino, $(C_1-C_6)$alkanoylamino, $(C_1-C_6)$alkoxycarbonyl, di-$(C_1-C_6)$alkylcarbamoyl, morpholinocarbonyl, and $(C_1-C_6)$alkylsulfonyl.

In some embodiments of the compounds of Formula (ID), M is —$CH_2$—.

In certain embodiments of the compounds of Formula (ID), $R^2$ is H. In some embodiments of the compounds of Formula (ID), $R^1$ and $R^3$ are independently H or halo.

In certain embodiments of the compounds of Formula (ID), $R^5$, $R^6$, and $R^7$ are independently H or halo.

In specific embodiments of the compounds of Formula (ID), M is —$CH_2$—; $R^2$ is H; $R^1$ and $R^3$ are independently H or halo; and $R^5$, $R^6$, and $R^7$ are independently H or halo. In specific instances of such embodiments, $R^1$ and $R^3$ are H; and $R^5$, $R^6$, and $R^7$ are independently H.

In a specific embodiment, the compound of the Formula (ID) is the compound of Formula 62, which has been found to have activity yielding a Ki value of 0.7 nM as determined by the assay described in Example 25, below.

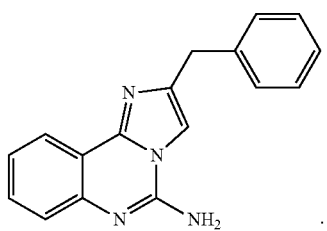

62

Methods for Making the Compounds of Formula (I)

The compounds of Formula (I) may be prepared from known or readily prepared starting materials, following methods known to one skilled in the art of organic synthesis. Methods useful for making the compounds of Formula (I) are set forth in the Schemes and Examples below. Alternative synthetic pathways and analogous structures will be apparent to those skilled in the art of organic synthesis. All stereoisomers and tautomeric forms of the compounds are contemplated.

The starting materials and reagents described in the Examples and in the schemes below are either available from commercial suppliers such as Sigma-Aldrich (St. Louis, Mo.) and Acros Organics Co. (Fair Lawn, N.J.), or can be prepared using methods well-known to one skilled in the art of organic synthesis.

One skilled in the art of organic synthesis will also recognize that the synthesis of Fused Tricyclic compounds of Formula (I) may require protection of certain functional groups (i.e., derivatization for the purpose of chemical compatibility with a particular reaction condition). Suitable protecting groups for the various functional groups of these compounds and methods for their installation and removal can be found in Greene et al., *Protective Groups in Organic Synthesis*, Wiley-Interscience, New York, (1999).

The starting materials used and the intermediates prepared using the methods set forth in the schemes above may be isolated and purified if desired using conventional techniques, including but not limited to filtration, distillation, crystallization, chromatography and the like. Such materials can be characterized using conventional means, including physical constants and spectral data.

The preparation of the compounds of the Formula (IA) (wherein D, M, W, $R^1$, $R^2$, and $R^3$ are as described above for the compound of the Formula I(A)) is illustrated in Scheme 1 below. Reaction of dichloride intermediate Int-IA with hydrazine yields quinoxaline Int-IIA. Quinoxaline Int-IIA can then be condensed with aldehyde D-M'-CHO (wherein M' is M ($CH_2$)) and subsequently reduced with a reducing agent such as sodium cyanoborohydride to give quinoxaline Int-IIIA. Quinoxaline Int-IIIA can then be cyclized to give Int-IVB with phosgene or an equivalent reagent. Subsequent reaction of Int-IVB with an amine ($R^2NH_2$) or ammonia at elevated temperature then provides compounds of the Formula (IA).

Scheme 1

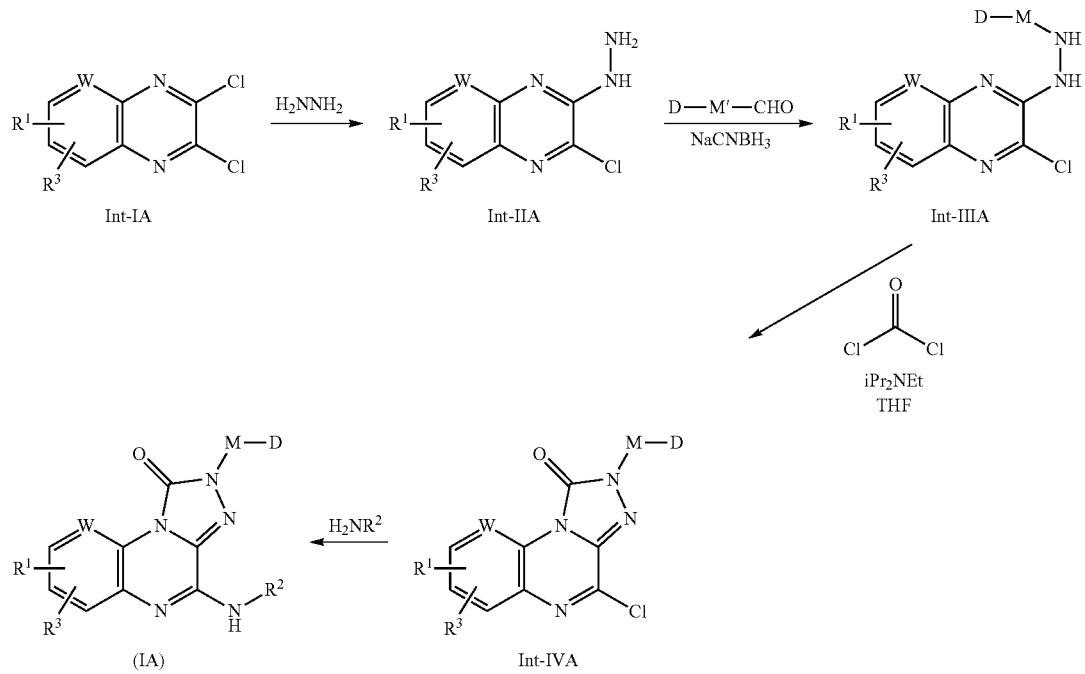

The preparation of compounds of Formula (IB) (wherein D, M, W R¹, R², and R³ are as described above for the compound of the Formula (IB)) is illustrated in Scheme 2. Reaction of dichloride Int-IA with an appropriate aminoalcohol yields amino-quinoxaline Int-IIB. This condensation is typically carried out at about 100° C. in the presence of 4-dimethylaminopyridine. The amino quinoxaline Int-IIB may then be cyclized to provide the tricycle Int-IIIB with reagents such as methanesulfonyl chloride in the presence of triethylamine. Tricycle Int-IIIB may then be oxidized, such as with $MnO_2$ in toluene at reflux to provide Int-IVA. Subsequent reaction of Int-IVA with an amine ($R^2NH_2$) or ammonia at elevated temperature then provides the compounds of Formula (IB).

-continued

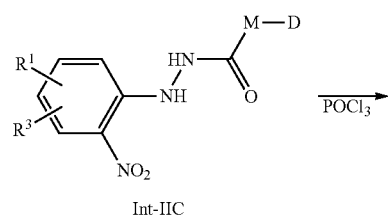

Int-IIC

Scheme 2

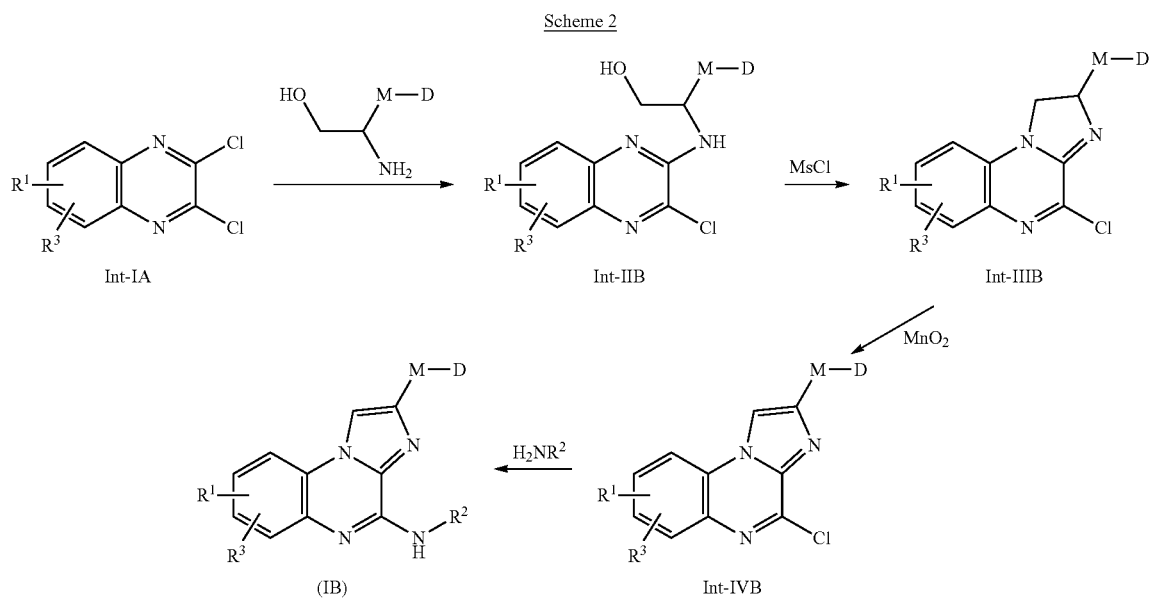

The preparation of compounds of the Formula (IC) (wherein D, M, W, R¹, R², and R³ are as described above for the compound of the Formula (IC)) is illustrated in Scheme 3 below. Acylation of phenylhydrazine Int-IC under suitable conditions yields hydrazide Int-IIC. Reaction of Int-IIC with $POCl_3$ at reflux yields Int-IIIC, and exposure of this intermediate to ammonia at room temperature yields aminoamidine Int-IVC. Cyclization of aminoamidine Int-IVC with ethyl chlorooxalate in toluene at reflux yields triazole Int-VC. Reduction of Int-VC using for example iron in acetic acid yields tricycle Int-VIC. Reaction of Int-VIC with $POCl_3$ at reflux yields chloride Int-VIIC. Subsequent reaction of chloride Int-VIIC with an amine ($R^2NH_2$) or ammonia at elevated temperature provides compounds of the Formula (IC).

-continued

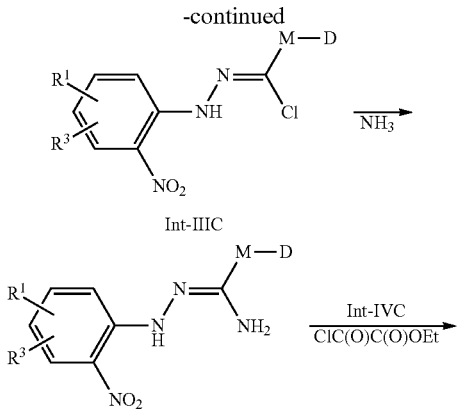

Scheme 3

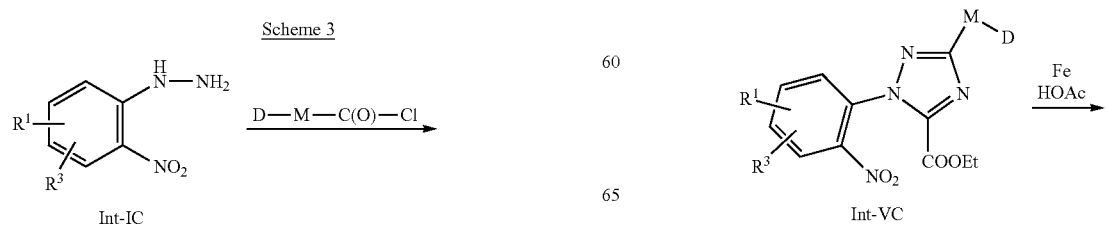

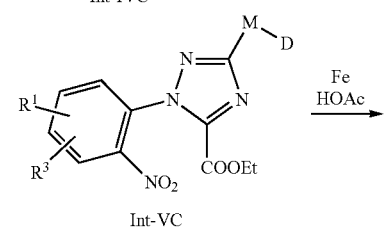

-continued

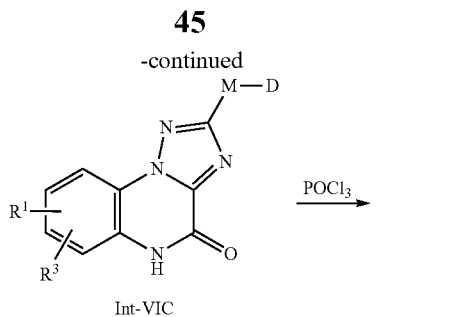

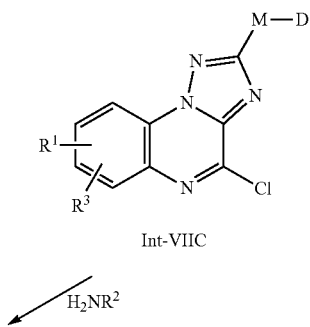

The preparation of compounds of Formula (ID) (wherein D, M, W, $R^1$, $R^2$, and $R^3$ are as described above for the compound of the Formula (ID)) is carried out analogously to the compounds of the Formula (IB) and is illustrated in Scheme 4 below. The starting dichloride Int-ID is converted via intermediates Int-IID, Int-IIID, and Int-IVD to the desired product in analogy to the sequence illustrated in Scheme 2 above from Int-IA via Int-IIB, Int-IIIB, and Int-IVB.

Scheme 4

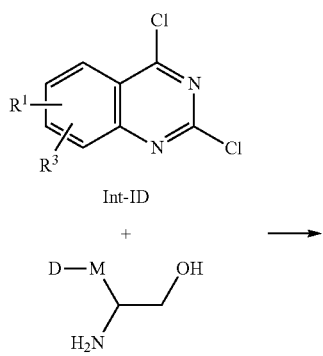

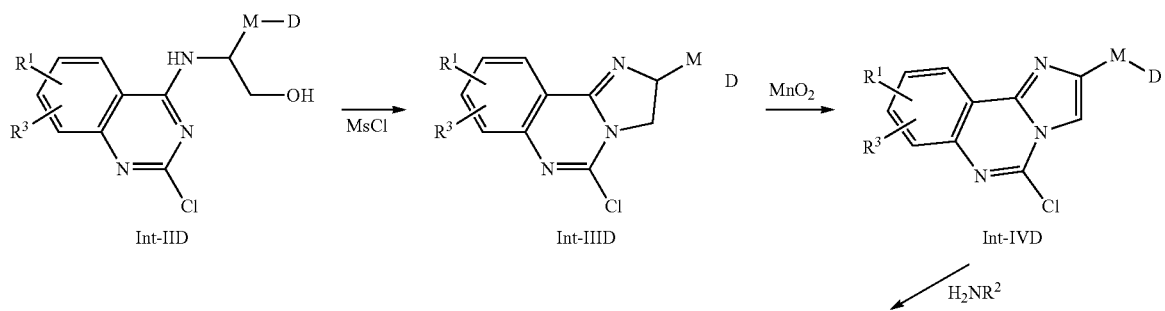

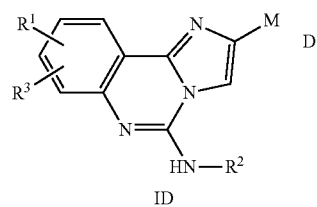

Compounds of the of the Formula (I) that incorporate deuterium atoms can be prepared from commercially available or known deuterium-containing reagents using modifications of the procedures described above. For instance, compounds of the Formula (IA) which contain deuterium on ring D can be prepared as shown schematically below in Scheme 5, which is a modification of the procedure described in Scheme I.

CH₃CN, 7 min—95% CH₃CN, 7.5 min—10% CH₃CN, 9 min—stop. The observed parent ions are given.

Example 1

Preparation of Quinoxaline and Pyridopyrazine Intermediates Useful in Making Compounds of Formula (IA)

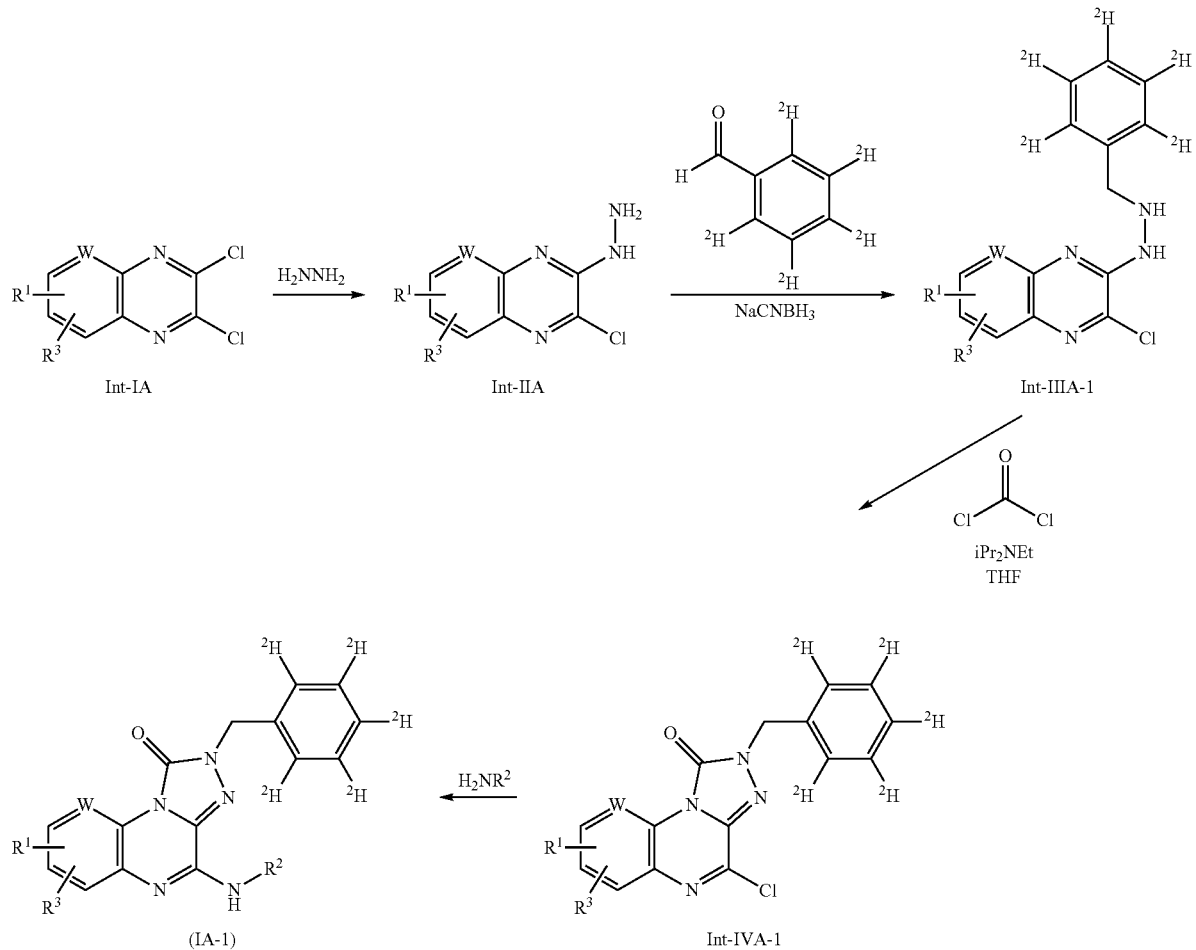

EXAMPLES

General Methods

Solvents, reagents, and intermediates that are commercially available were used as received. Reagents and intermediates that are not commercially available were prepared in the manner as described below. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min—10% CH₃CN, 5 min—95%

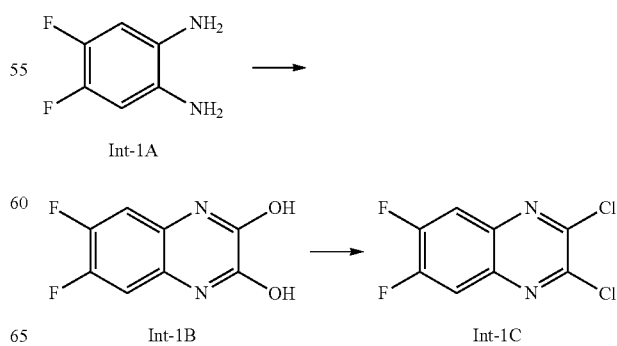

The preparation of dichloro-difluoroquinoxaline Int-1C is used to illustrate the method.

Step A—Preparation of Int-1B

Int-1A (2.00 g, 13.9 mmol) and diethyl oxalate (30 mL) were combined, heated at reflux for 18 h, allowed to cool, diluted with hexane (30 mL), and filtered. Chromatography on silica gel gave Int-1B as a red-black solid.

Step B—Preparation of Int-1C

Int-1B (1.50 g, 7.6 mmol) and POCl$_3$ (10 mL) were combined, heated at reflux for 18 h, allowed to cool, and concentrated. The residue was treated with ice-water, stirred for 0.5 h, and filtered. Chromatography on silica gel (3% MeOH/ CH$_2$Cl$_2$) gave Int-1C as a yellow solid. For the preparation of certain analogous intermediates, SOCl$_2$ with catalytic DMF was employed to effect this conversion.

Using similar methods the following intermediates were prepared from the appropriate starting materials:

| Intermediate | structure | form |
|---|---|---|
| Int-1A-1 | (Me-substituted dichloroquinoxaline) | brown solid |
| Int-1A-2 | (O$_2$N-substituted dichloroquinoxaline) | off-white solid |
| Int-1A-3 | (MeOOC-substituted dichloroquinoxaline) | yellow solid |
| Int-1A-4 | (F$_3$C-substituted dichloroquinoxaline) | brown solid |
| Int-1A-5 | (F-substituted dichloroquinoxaline) | gray solid |
| Int-1A-6 | (MeO-substituted dichloroquinoxaline) | green solid |
| Int-1A-7 | (dichloropyridopyrazine) | brown solid |

Example 2

Conversion of Quinoxaline and Pyridopyrazine Intermediates of Example 1 to Tricyclic Compounds of the Formula (IA)

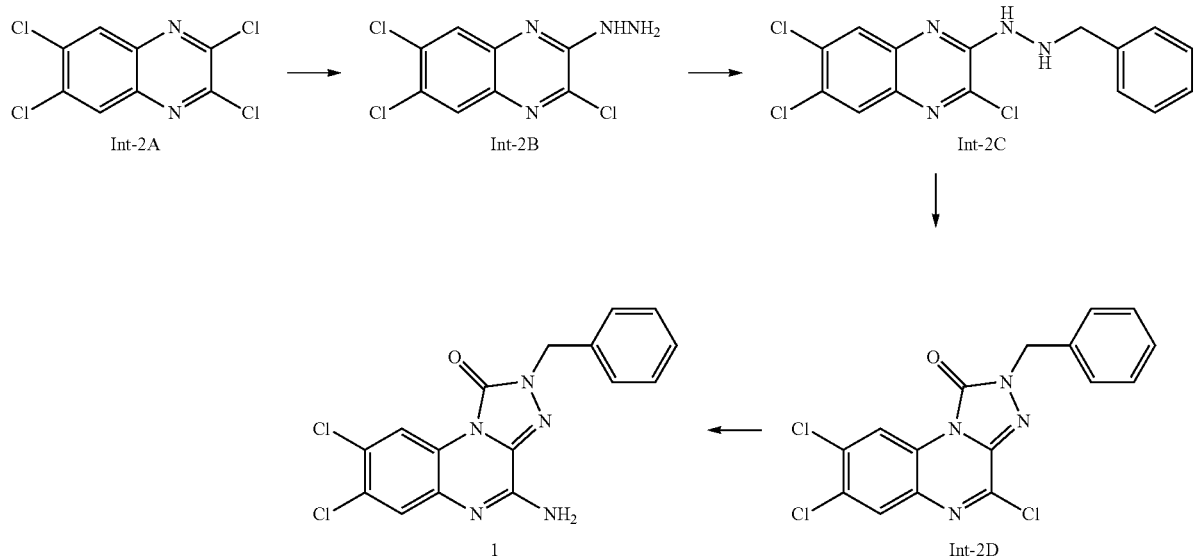

Step A—Synthesis of Int-2B

Int-2A (1.00 g, 3.7 mmol) and hydrazine hydrate (0.27 mL, 8.6 mmol) were dissolved in EtOH (20 mL) and the mixture stirred 22 h. The resulting solid was filtered and washed with EtOH to provide Compound Int-2B as a yellow solid.

Step B Synthesis of Int-2C

To Int-2B (0.600 g, 2.3 mmol) in CH$_2$Cl$_2$ (40 mL) were added AcOH (0.10 mL) and then benzaldehyde (0.23 mL, 2.3 mmol). The mixture was stirred for 2 h, and NaCNBH$_3$ (0.36 g, 5.7 mmol) was added. After 3 h stirring, the mixture was partitioned with CH$_2$Cl$_2$ and water. Drying (MgSO$_4$), concentration, and purification by PLC provided Int-2C as a yellow solid.

Step C—Synthesis of Int-2D

Int-2C (0.22 g, 0.63 mmol), 20% phosgene in toluene (0.43 mL, 0.81 mmol) and DIPEA (0.14 mL, 0.81 mmol) were combined in THF (4.0 mL) at 0° C. The mixture was stirred 1 h, concentrated, and treated with MeOH. Filtration gave Int-2D as a yellow solid.

Step D—Synthesis of Compound 1

Int-2D (0.10 g, 0.26 mmol) in EtOH (2.0 mL) was treated with 2.0 M ammonia in EtOH (1.3 mL, 2.6 mmol). The mixture was heated in a sealed tube at 120° C. for 18 h, allowed to cool, concentrated and purified by PLC to yield Compound 1 as a yellow solid, LC/MS: m/e 360, 362, 364 (M+H).

In similar fashion, the following compounds reported in Table I were prepared from the appropriate starting materials: Compounds 1 to 4; Compounds 6 to 10; Compounds 12 to 15; Compounds 17 to 22; Compound 24, Compounds 26 to 30; Compounds 36 and 37; Compounds 41 to 45; and Compounds 47, 50, 51, 55 and 56. Each of the aforementioned compounds was characterized by mass spectroscopy, and their mass, expressed as an M/e value, is reported in Table 1, above.

Example 3

Preparation of Compound 5

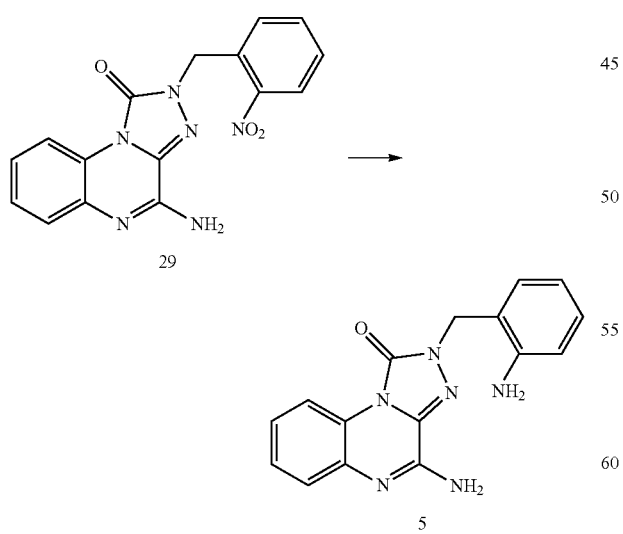

Compound 29 (0.106 g, 0.32 mmol) and iron powder (0.132 g, 2.3 mmol) were combined in 80% EtOH (6 mL) and AcOH (6 mL) and stirred for 0.25 h. Conc. HCl (6 drops) was added and the mixture heated at reflux 0.5 h. On cooling, the solid was filtered, and the filtrate was concentrated and treated with MeOH (5 mL). The solid was filtered and purified by chromatography on silica gel to provide Compound 5 as an off-white solid, LC-MS: 307 (M+H).

Example 4

Preparation of Compound 11

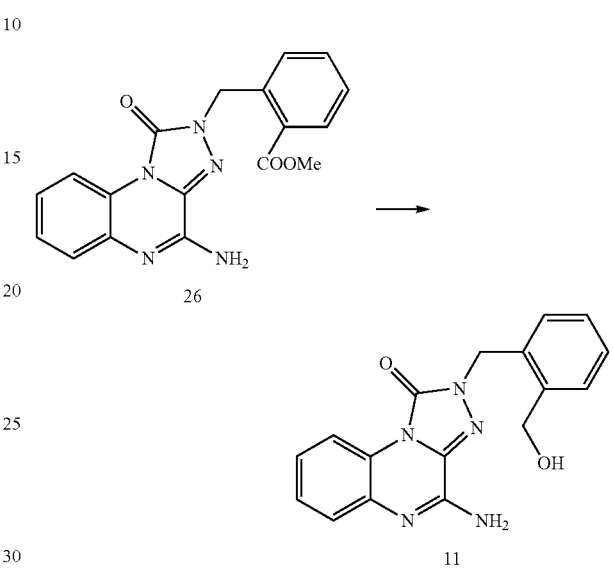

Compound 26 (0.050 g, 0.14 mmol) was dissolved in THF (5.0 mL), and LiAlH$_4$ (0.016 g, 0.43 mmol) was added. The mixture was stirred for 2 h, concentrated, and purified by PLC to provide Compound 11 as a yellow solid, LC-MS: 322 (M+H).

Example 5

Preparation of Compound 23

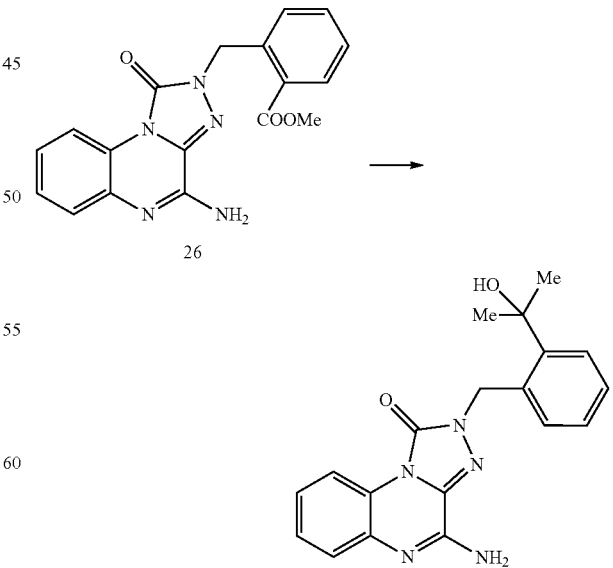

Compound 26 (0.039 g, 0.11 mmol) was dissolved in THF (5.0 mL), and 3.0 M MeMgBr in ether (0.11 mL, 034 mmol) was added. The mixture was stirred for 2 h, concentrated, and purified by PLC to provide Compound 23 as a yellow solid, LC-MS: 350 (M+H).

Example 6

Step A—Synthesis of Compound 40

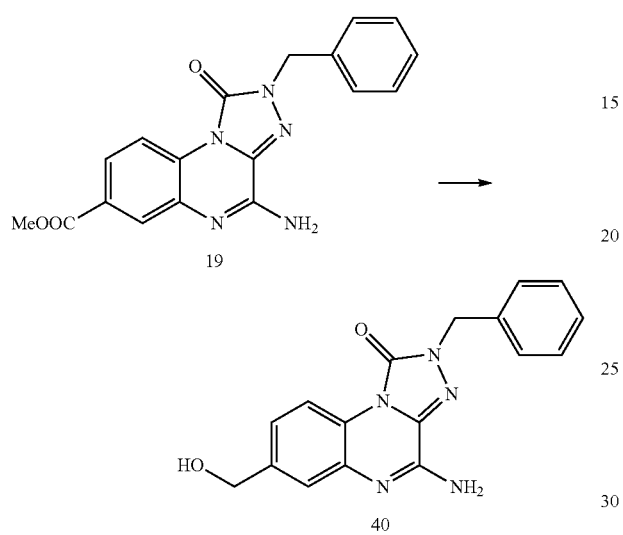

Compound 19 (0.356 g, 1.02 mmol) in $CH_2Cl_2$ (40 mL) was cooled to −78° C. and treated with DIBAL-H (25% in toluene, 2.1 mL, 3.1 mmol), and stirred at −78° C. for 3 h. The reaction was allowed to warm, quenched with water, extracted with $CH_2Cl_2$, dried ($MgSO_4$), and concentrated. The residue was dissolved in THF (20 mL), cooled to 0° C., and treated with $LiAlH_4$ (0.040 g, 1.0 mmol). The mixture was stirred for 2 h, treated with water (50 mL), extracted with $CH_2Cl_2$, dried ($MgSO_4$), and concentrated to provide compound 40 as a yellow solid, LC-MS: 322 (M+H).

Step B—Synthesis of Compound 25

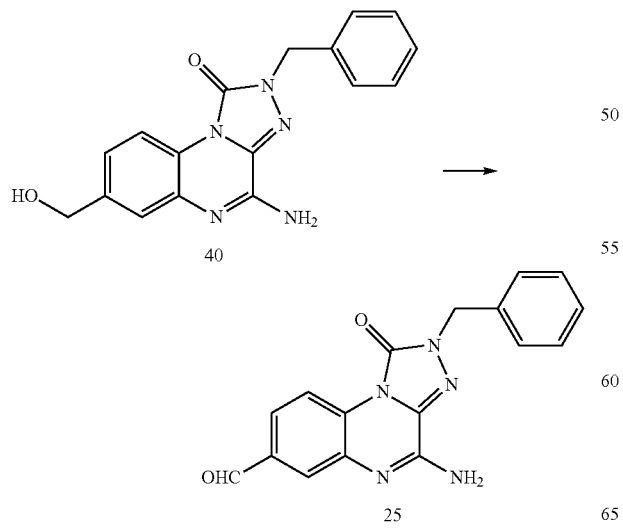

Compound 40 (0.306 g, 0.95 mmol) was combined with $MnO_2$ (0.83 g, 9.5 mmol) in $CH_2Cl_2$ (30 mL). The mixture was stirred for one week, filtered, concentrated, and purified by PLC to provide Compound 25 as a white solid, LC-MS: 320 (M+H).

Example 7

Preparation of Compound 52

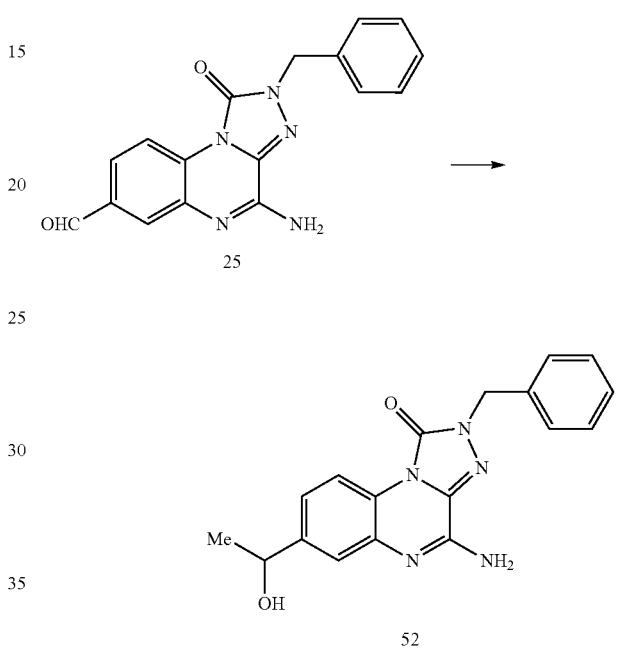

Compound 25 (0.11 g, 0.35 mmol) was dissolved in THF (12 mL), and cooled to 0° C. 1.0 M MeMgBr in ether (1.0 mL, 1.0 mmol) was added and the mixture stirred for 2 h, allowed to warm, and treated again with 1.0 M MeMgBr in ether (0.50 mL, 0.5 mmol). After 1 h, the reaction was partitioned with $CH_2Cl_2$ and water, dried ($MgSO_4$), and concentrated to provide Compound 52 as a yellow solid, LC-MS: 336 (M+H).

Example 8

Preparation of Compound 31

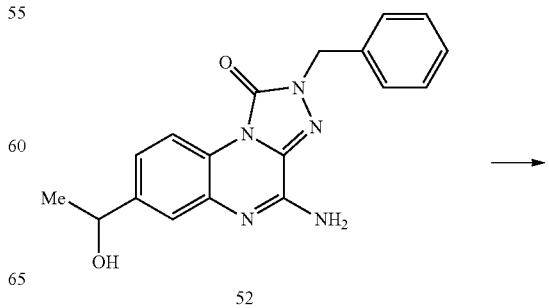

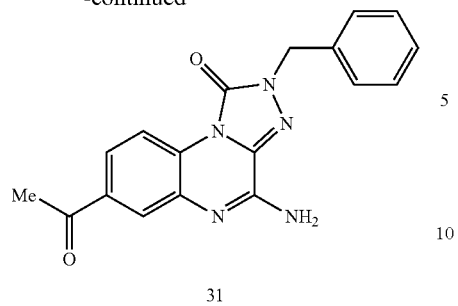

31

Compound 52 (0.080 g, 0.24 mmol) was combined with pyridinium chlorochromate (0.52 g, 2.39 mmol) in CH$_2$Cl$_2$ (10 mL). The mixture was stirred for 6 h, filtered, and concentrated to provide Compound 31 as a white solid, LC-MS: 334 (M+H).

Example 9

Preparation of Compound 33

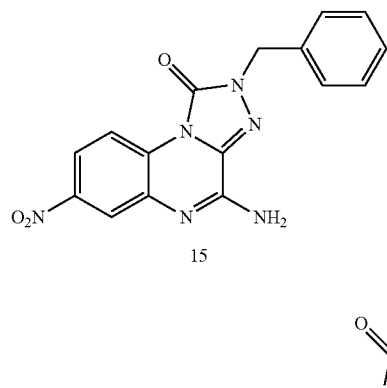

Compound 15 was reduced according to the procedure of Example 3 to provide
Compound 33 as a yellow solid, LC-MS: 307 (M+H).

Example 10

Preparation of Compound 34

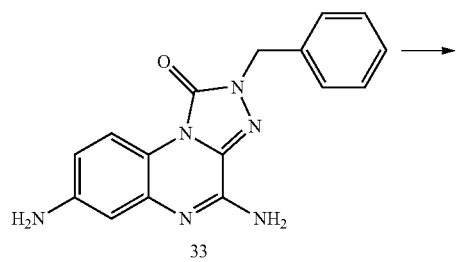

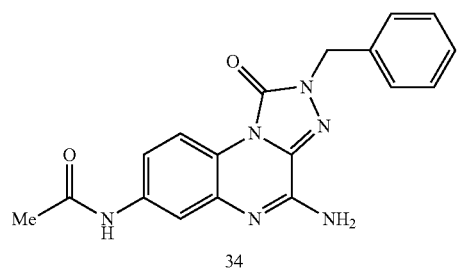

34

Compound 33 (0.033 g, 0.11 mmol), acetyl chloride, (0.009 mL, 0.13 mmol) and DIPEA (0.028 mL, 0.16 mmol) were combined in DMF (4.0 mL). The mixture was stirred for 1 h, concentrated, and purified by PLC to provide Compound 34 as an off-white solid, LC-MS: 349 (M+H).

Example 11

Preparation of Compound 38

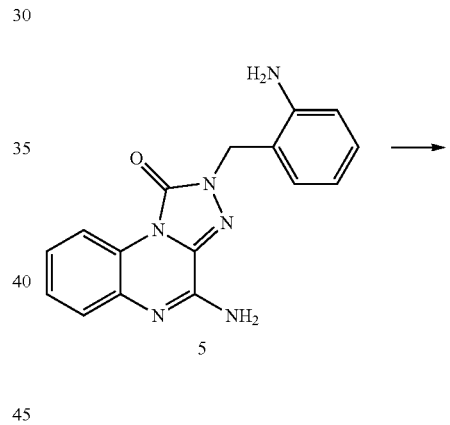

According to the procedure of Example 10, Compound 5 was converted to Compound 38, an off-white solid, LC-MS: 349 (M+H).

Example 12

Preparation of Compound 39

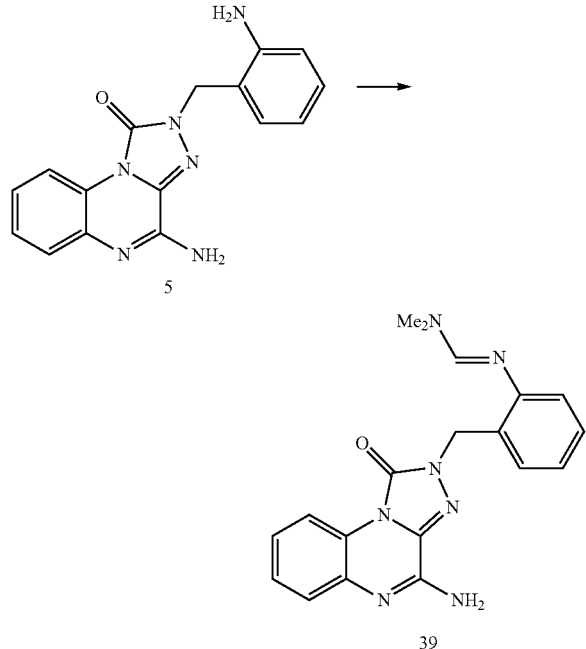

Reaction of Compound 5 with methyl chloroformate in DMF provided Compound 39 as a white solid, LC-MS: 362 (M+H).

Example 13

Preparation of Compound 48

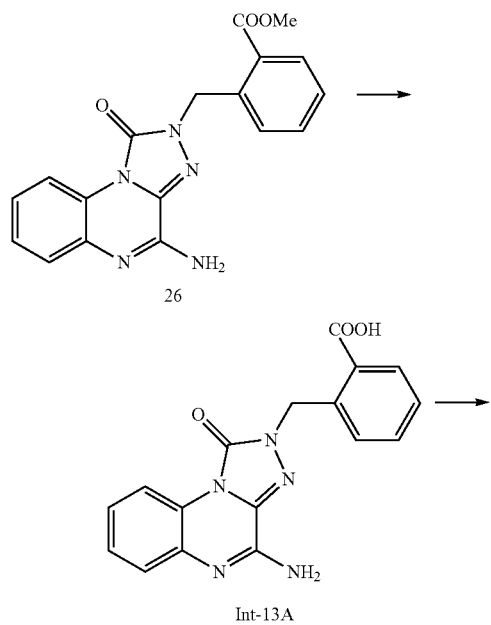

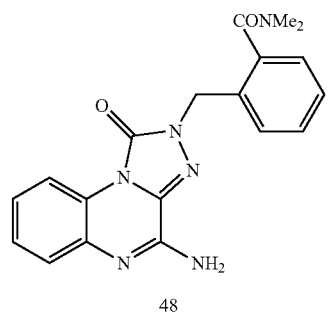

Step A—Synthesis of Int-13A

To a suspension of Compound 26 (0.32 g, 0.92 mmol) in EtOH (5 mL) was added 1.0N NaOH (3.67 mL, 3.67 mmol). The mixture was stirred for 18 h, and 1.0 N HCl (4.0 mL) was added. Filtration gave Compound Int-13A as a white solid.

Step B—Synthesis of Compound 48

To Int-13A (0.085 g, 0.25 mmol) in DMF (3.0 mL) were added 2.0 M dimethylamine in THF (0.19 mL, 0.38 mmol), EDCI (0.058 g, 0.30 mmol), HOBt.H₂O, (0.041 g, 0.30 mmol) and N-methylmorpholine (0.033 mL, 0.30 mmol). The mixture was stirred 18 h, concentrated, and purified by PLC to provide Compound 48 as a white solid, LC-MS: 363 (M+H).

Example 14

Preparation of Compound 49

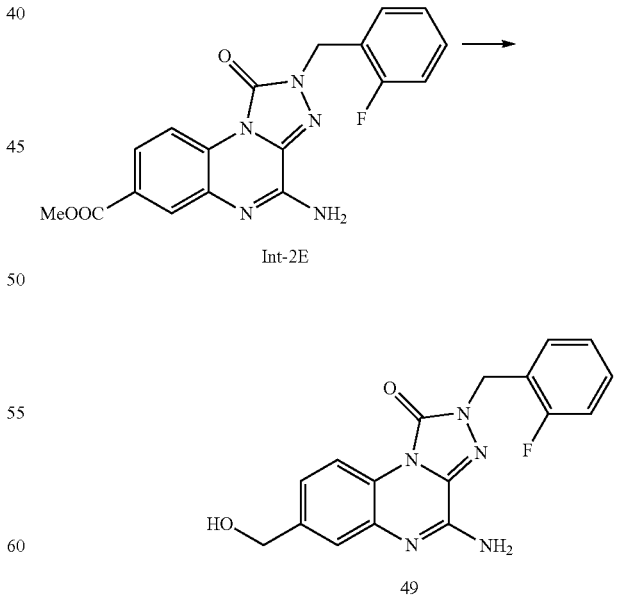

In similar fashion to Example 6, Int-2E was converted to compound 49, a yellow solid, LC-MS: 340 (M+H).

Example 15

Preparation of Compound 53

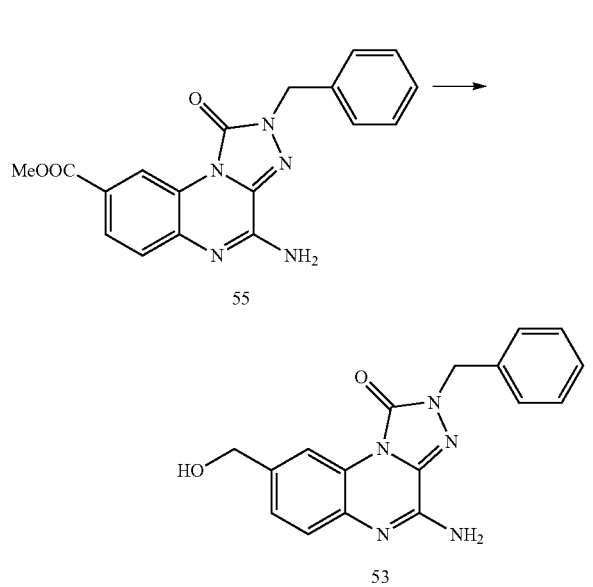

In similar fashion to Example 6, compound 55 was converted to Compound 53, a yellow solid, LC-MS: 322 (M+H).

Example 16

Preparation of Compound 54

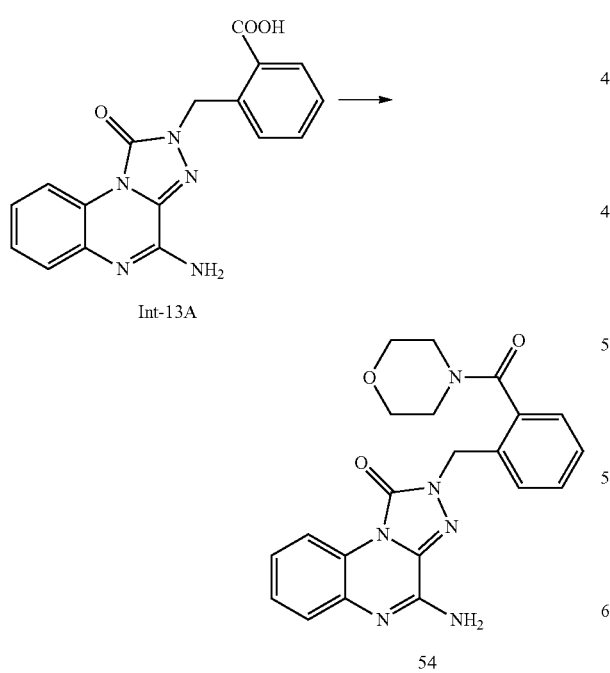

In similar fashion to Example 13, Step B, but with morpholine in place of dimethylamine, Int-13A was converted to compound 54, a white solid, LC-MS: 405 (M+H).

Example 17

Preparation of Compound 46

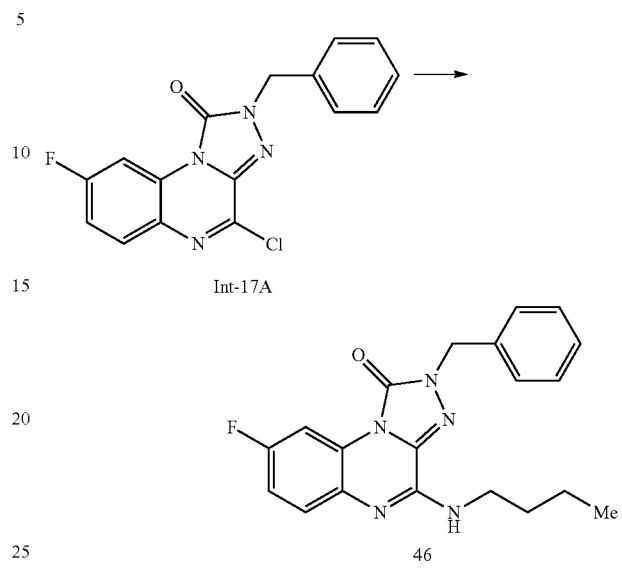

Int-17A was prepared in a similar fashion as was used to synthesize Int-2D using Steps A-C of Example 1 Int-17A (100 mg, 0.30 mmol), Et$_3$N (0.064 mL, 0.046 mmol) and butylamine (0.045 mL, 0.46 mmol) were combined in EtOH (2 mL) and the mixture was heated in microwave for 1 h at 85° C. The mixture was concentrated in vacuo and purified by PLC to provide compound 46: LC-MS: 366.2 (M+H).

Example 18

Preparation of Compounds 35 and 32

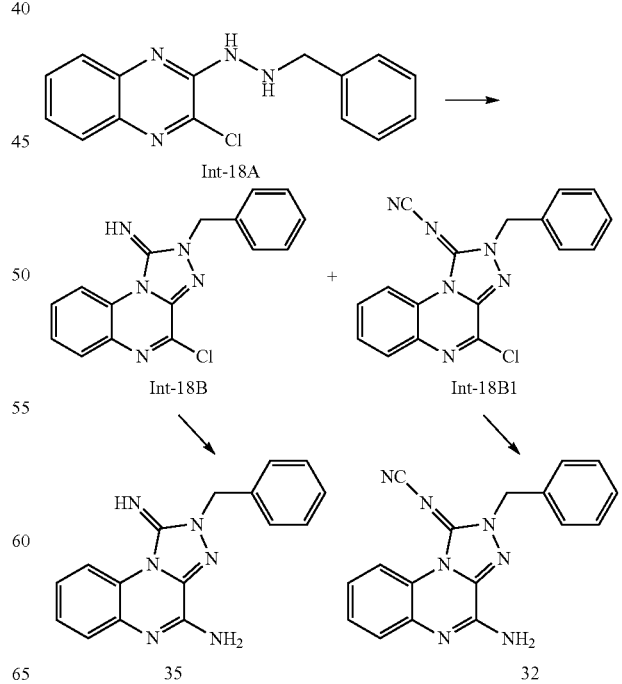

Step A—Synthesis of Int-18B and Int-18B1

Int-18A was prepared analogously to Int-2C. This material (0.25 g, 0.88 mmol) was combined with DIPEA (0.31 mL, 1.76 mmol) in $CH_2Cl_2$ (4.0 mL) The solution was cooled to 0° C., and BrCN (5.0 M in MeCN, 0.35 mL, 1.76 mmol) was added. The mixture was stirred for 1 h, allowed to warm, and stirred 18 h. The mixture was concentrated, taken up in isopropanol (20 mL), and heated at 60° C. for 1 h. Concentration and PLC provided Int-18B and Int-18B1, each as a yellow solid.

Step B—Synthesis of Compound 35

Int-18B (0.065 g, 020 mmol) was combined with 2.0 M ammonia in isopropanol (3.0 mL) and heated in a sealed tube at 110° C. 1 h, then cooled to 0° C. Filtration yielded compound 35 as a yellow solid, LC-MS: 291 (M+H).

Step B1—Synthesis of Compound 32

Int-18B1 (0.032 g, 0.096 mmol) was treated in identical fashion to Int-18B in Step B to provide compound 32 as a white solid, LC-MS: 316 (M+H).

Example 19

Preparation of Compound 57

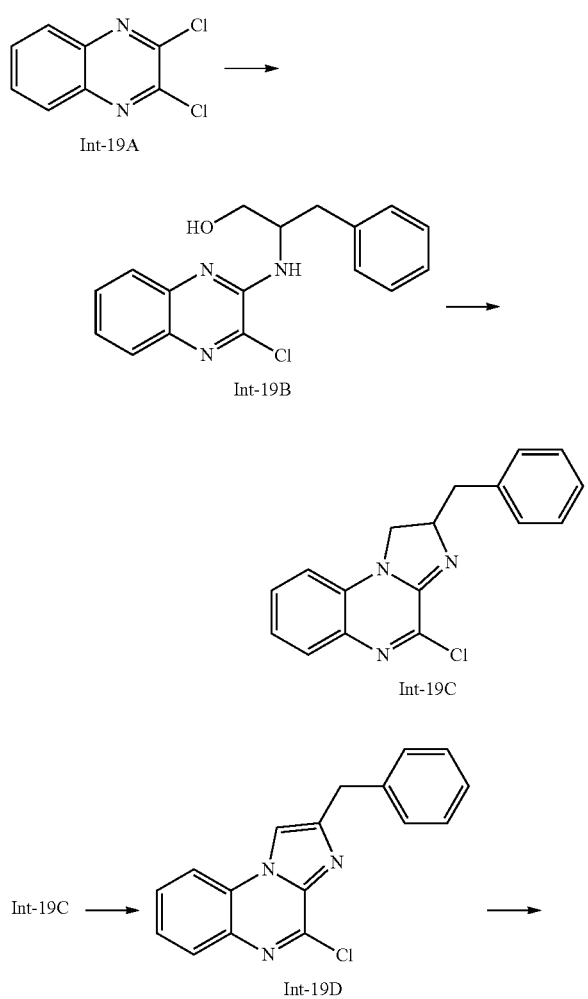

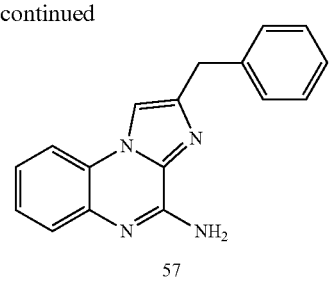

Step A—Synthesis of Int-1913

Int-19A (3.00 g, 15.1 mmol) was combined with DL-2-amino-3-phenyl-1-propanol (3.49 g, 22.6 mmol), DIPEA (5.25 mL, 30 mmol) and 4-dimethylaminopyridine (0.18 g, 1.5 mmol) in DMF (20 mL), heated at 100° C. for 4 h, and allowed to cool. The mixture was partitioned with EtOAc and water, and washed with water, then brine. Drying ($MgSO_4$), concentration, and chromatography on silica gel gave Int-19B as an orange oil.

Step B—Synthesis of Int-19C

To Int-19B (0.400 g, 1.28 mmol) in $CH_2Cl_2$(10 mL) was added $Et_3N$ (0.267 mL, 1.91 mmol), followed by methanesulfonyl chloride (0.128 mL, 1.66 mmol). The mixture was stirred for 1 h, concentrated, and purified by PLC to provide Int-19C as a yellow gum.

Step C—Synthesis of Int-19D

Compound Int-19C (0.13 g, 0.44 mmol) was combined with $MnO_2$ (0.38 g, 0.44 mmol) in toluene (5 mL). The mixture was heated at reflux for 20 h, and additional $MnO_2$ (0.76 g, 0.88 mmol) was added. After another 24 h, the addition of $MnO_2$ was repeated. After another 24 h, the mixture was allowed to cool and filtered. Concentration and purification by PLC yielded Int-19D as a brown oil. This oxidation was also achieved with 10% Pd/C instead of $MnO_2$.

Step D—Preparation of Compound 57

Int-19D (0.095 g, 0.32 mmol) was combined with 2 M ammonia in EtOH (4.0 mL) and heated in a sealed tube at 100° C. for 20 h. Concentration and purification by PLC gave compound 57 as an off-white solid, LC-MS: 275 (M+H).

Example 20

Preparation of Compound 58

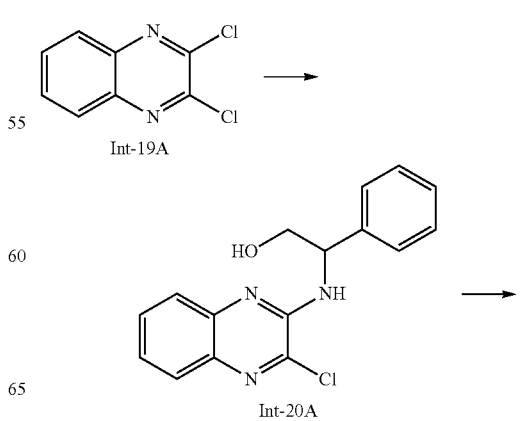

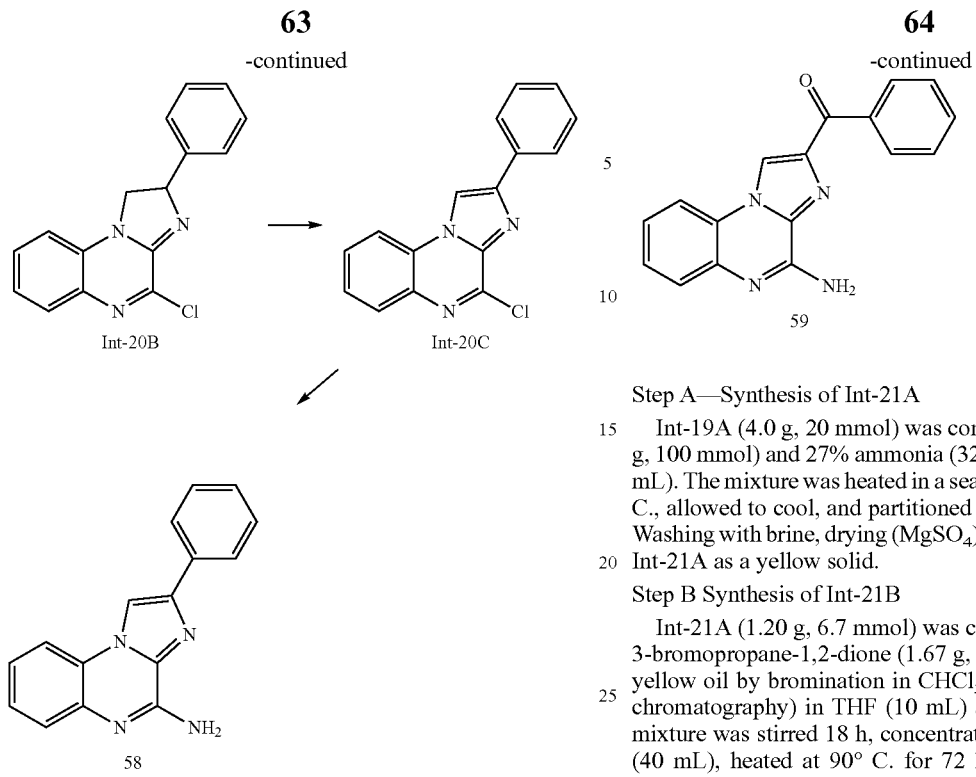

In similar fashion to Example 19, starting with Int-19A and 2-amino-2-phenylethanol, compound 58 was obtained as a white solid, LC-MS: 261 (M+H).

Example 21

Preparation of Compound 59

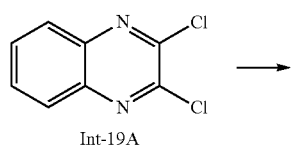

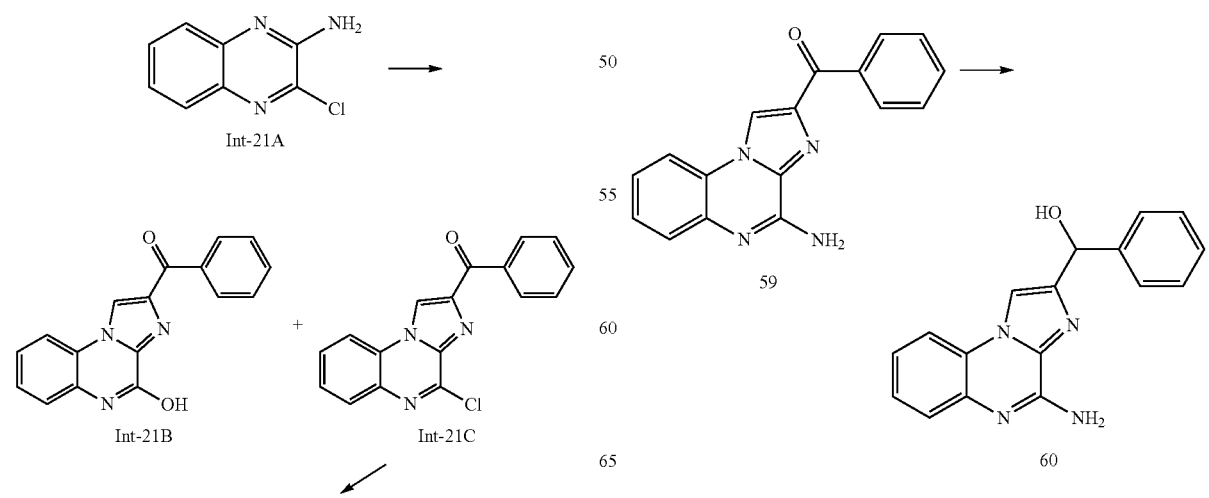

Step A—Synthesis of Int-21A

Int-19A (4.0 g, 20 mmol) was combined with NH₄Cl (5.4 g, 100 mmol) and 27% ammonia (32 mL) in isopropanol (40 mL). The mixture was heated in a sealed vessel for 20 h at 80° C., allowed to cool, and partitioned with CH₂Cl₂ and water. Washing with brine, drying (MgSO₄), and concentration gave Int-21A as a yellow solid.

Step B Synthesis of Int-21B

Int-21A (1.20 g, 6.7 mmol) was combined with 1-phenyl-3-bromopropane-1,2-dione (1.67 g, 7.4 mmol, prepared as a yellow oil by bromination in CHCl₃ at 50° C., followed by chromatography) in THF (10 mL) and ether (15 mL). The mixture was stirred 18 h, concentrated, treated with ethanol (40 mL), heated at 90° C. for 72 h, and allowed to cool. Concentration, addition of methanol (10 mL), and filtration gave Int-21B as a brown solid.

Step C—Synthesis of Int-21C

Int-21B (0.20 g, 0.69 mmol) was combined with POCl₃ (8 mL), heated at 105° C. for 18 h, concentrated, and treated with water (10 mL). Filtration gave Compound Int-21C as a brown solid.

Step D—Synthesis of Compound 59

Int-21C (0.19 g, 0.63 mmol) was combined with 2 M ammonia in isopropanol (20 mL), heated in a sealed tube for 24 h at 110° C., concentrated and filtered. Purification of the solid by PLC gave compound 59 as a brown solid, LC-MS: 289 (M+H).

Example 22

Preparation of Compound 60

To compound 59 (0.025 g, 0.087 mmol) in THF (5 mL) was added NaBH$_4$ (0.010 g, 0.26 mmol). The mixture was stirred for 18 h, treated with MeOH, concentrated, and purified by PLC to give compound 60 as an off-white solid, LC-MS: 291 (M+H).

Example 23

Preparation of Compound 61

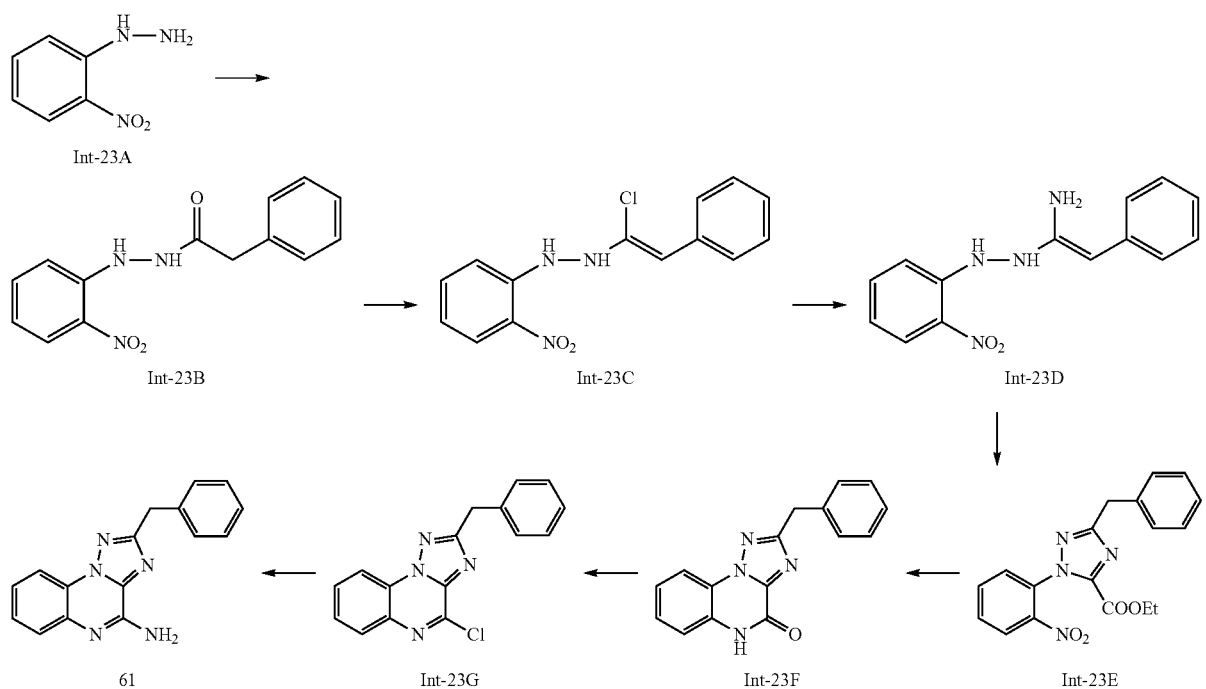

Step A—Synthesis of Int-23B

To Int-23A (2.00 g, 13.1 mmol) in CH$_2$Cl$_2$ (10 mL) was added N-methylmorpholine (1.87 mL, 17.0 mmol), followed by phenylacetyl chloride (1.85 mL, 14.0 mmol). The reaction was stirred for 0.5 h and partitioned with CH$_2$Cl$_2$ and water. Washing with brine, drying (MgSO$_4$), concentration, and chromatography on silica gave Int-23B as a brown solid.

Step B—Synthesis of Int-23C

Int-23B (0.80 g, 3.0 mmol) was combined with POCl$_3$ (15 mL), heated at 110° C. for 2 h, and poured onto ice-water (100 mL). After 0.5 h stirring, the mixture was extracted with CH$_2$Cl$_2$. Washing with brine, drying (MgSO$_4$), and concentration gave Int-23C as a brown oil.

Step C—Synthesis of Int-23D

Int-23C (0.31 g, 1.1 mmol) was combined with 2 M ammonia in isopropanol (15 mL), sealed, allowed to stand for 18 h, and concentrated. Partitioning with CH$_2$Cl$_2$ and water, washing with brine, drying (MgSO$_4$), and concentration gave Int-23D as a brown oil.

Step D—Synthesis of Int-23E

To Int-23D (0.27 g, 1.0 mmol) in ether (6 mL) was added dropwise ethyl oxalyl chloride (0.35 mL, 3.1 mmol) in ether (6 mL). Toluene (12 mL) was added, the ether removed, and the mixture heated at 110° C. for 3 h, and concentrated. Purification by PLC gave Int-23E as a brown oil.

Step E—Synthesis of Int-23F

To Int-23E (0.12 g, 0.33 mmol) in HOAc (5 mL) was added iron powder (0.34 g, 6.0 mmol). The mixture was heated at 90° C. for 1 h, allowed to cool, filtered, and concentrated. Purification by PLC gave Int-23F as an off-white solid.

Step F—Synthesis of Int-23G

Int-23F (0.10 g, 3.0 mmol) was combined with POCl$_3$ (6 mL), heated at 110° C. for 72 h, concentrated, and poured onto ice-water. The mixture was extracted with CH$_2$Cl$_2$. Washing with brine, drying (MgSO$_4$), concentration, and purification by PLC gave Int-23G as a white solid.

Step G—Synthesis of Compound 61

Int-23G (0.06 g, 0.2 mmol) was combined with 2 M ammonia in isopropanol (10 mL), sealed, heated at 90° C. for 64 h, concentrated, and treated with MeOH. Filtration gave compound 61 as a white solid, LC-MS: 276 (M+H).

Example 24

Preparation of Compound 62

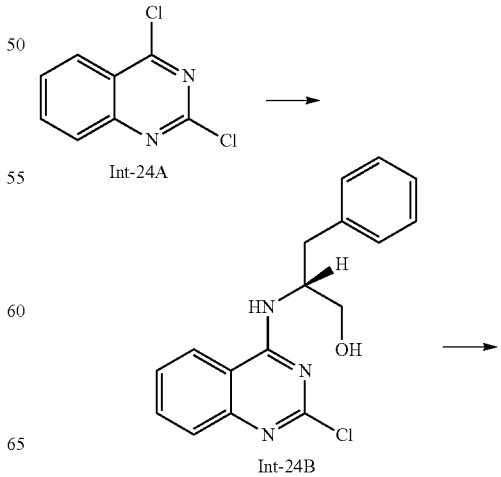

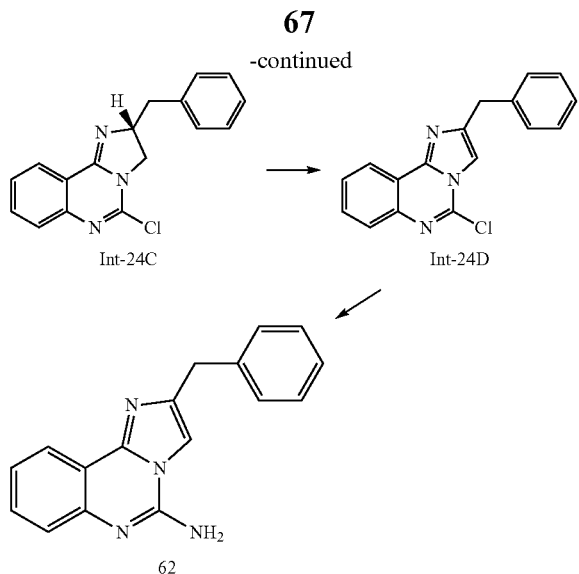

Step A—Synthesis of Int-24B

Int-24A (1.50 g, 7.5 mmol) was combined with R-2-amino-3-phenyl-1-propanol (1.74 g, 11.5 mmol), DIPEA (2.63 mL, 15.1 mmol) and 4-dimethylaminopyridine (0.092 g, 0.75 mmol) in DMF (10 mL), heated at 100° C. for 1 h, and allowed to cool. Concentration and chromatography on silica gel gave Int-24B as an off-white solid.

Step B—Synthesis of Int-24C

To Int-24B (0.25 g, 0.80 mmol) in $CH_2Cl_2$ (10 mL) was added $Et_3N$ (0.17 mL, 1.2 mmol), followed by methanesulfonyl chloride (0.080 mL, 1.03 mmol). The mixture was stirred for 18 h, and the addition of $Et_3N$ and methanesulfonyl chloride were repeated. After 1 h, the mixture was concentrated and purified by PLC to provide Int-24C as a colorless gum.

Step C—Synthesis of Int-24D

Int-24C (0.24 g, 0.081 mmol) was combined with $MnO_2$ (0.35 g, 0.41 mmol) in toluene (10 mL). The mixture was heated at reflux for 20 h, and additional $MnO_2$ (0.71 g, 0.82 mmol) was added. After another 24 h, the addition of $MnO_2$ was repeated. After another 24 h, the mixture was allowed to cool and filtered. Concentration and purification by PLC yielded Int-24D as a yellow oil.

Step D—Synthesis of Compound 62

Int-24D (0.045 g, 0.15 mmol) was combined with 2 M ammonia in isopropanol (10 mL) and heated in a sealed tube at 110° C. for 20 h. Concentration and purification by PLC gave compound 62 as an off-white solid, LC-MS: 275 (M+H).

The pharmacological activity of the compounds of the invention was determined by the following in vitro and in vivo assays to measure $A_{2a}$ receptor activity.

Example 25

Human Adenosine $A_{2a}$ Receptor Competition Binding Assay Protocol

Membrane Sources:

$A_{2a}$: Human $A_{2a}$ Adenosine Receptor membranes, Catalog #RB-HA2a, Receptor Biology, Inc., Beltsville, Md. Dilute to 17 µg/100 µl in membrane dilution buffer (see below).

Assay Buffers:

Membrane dilution buffer: Dulbecco's Phosphate Buffered Saline (Gibco/BRL)+ 10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligand:

$A_{2a}$: [3H]-SCH 58261 [7-(2-phenylethyl)-5-amino-2-(2-furyl)-pyrazolo-[4,3-e]-1,2,4-triazolo[1,5-c]pyrimidine], custom synthesis, Amersham Pharmacia Biotech, Piscataway, N.J. Stock is prepared at 1 nM in membrane dilution buffer. Final assay concentration is 0.5 nM. SCH-58261 is discussed in Zocchi et al., *J Pharmacol Exp Ther.* 276(2):398-404 (1996).

Non-Specific Binding:

$A_{2a}$: To determine non-specific binding, add 100 nM CGS 15923 (RBI, Natick, Mass.). Working stock is prepared at 400 nM in compound dilution buffer.

Compound Dilution:

Prepare 1 mM stock solutions of compounds in 100% DMSO. Dilute in compound dilution buffer. Test at 10 concentrations ranging from 3 µM to 30 µM. Prepare working solutions at 4× final concentration in compound dilution buffer.

Assay Procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl of drug working solution. Add 50 µl ligand stock ([3H]-SCH 58261 for $A_{2a}$. Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Ki values were determined for representative compounds of the present invention, i.e., compounds 1-62, using the above-described method. The compounds of the present invention had Ki values for the adenosine $A_{2a}$ receptor of 0.4 to 95 nM.

Example 26

Haloperidol-Induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 sec.

The selective $A_{2A}$ adenosine antagonists under evaluation are administered orally at a dose of 10 mg/kg, 1 and 4 h before scoring the animals relative to animals not treated with any adenosine antagonists. Compounds 2, 9, 17 30, and 40 were evaluated in this animal model. At the 1 h time point these compounds showed 26% to 50% inhibition, and at the 4 h time point, these compounds showed 43% to 56% inhibition relative to untreated animals.

In separate experiments, the anticataleptic effects of the reference compound, L-DOPA (25, 50 and 100 mg/kg, ip), were determined.

Uses of the Fused Tricyclic Compounds

The Fused Tricyclic Compounds are useful in human and veterinary medicine. For instance, in some embodiments the Fused Tricyclic groups are useful in therapeutic applications in human and veterinary medicine. In some embodiments, the Fused Tricyclic Compounds are useful in a method of antagonizing the adenosine $A_{2a}$ receptor in a patient such as a mammal in need of such antagonism comprising the administration of an effective amount of the compound.

While not being bound by any specific theory it believed that the Fused Tricyclic Compounds are useful in the treatment of depression, cognitive function diseases and neurodegenerative diseases such as Parkinson's disease, senile dementia as in Alzheimer's disease, psychoses of organic origin, attention deficit disorders, EPS, dystonia, RLS and PLMS because of their adenosine $A_{2a}$ receptor antagonist activity. In certain embodiments, the compounds of the present invention can improve motor-impairment due to neurodegenerative diseases such as Parkinson's disease.

The general value of the compounds of the invention in antagonizing the adenosine $A_{2a}$ receptor can be determined, for example, using the assays described above in Example 25. Alternatively, the general value of the compounds in treating disorders and diseases for human and animal use may be established in industry standard animal models for demonstrating the efficacy of compounds in treating CNS disorders, such as the haloperidol-induced catalepsy model described above in Example 26.

In some embodiments of the methods described above, a therapeutically effective amount of a pharmaceutically acceptable salt of the Fused Tricyclic Compound is administered. In specific embodiments, a therapeutically effective amount of a pharmaceutically acceptable salt of the Fused Tricyclic Compound is administered to the patient. In other specific embodiments, the Fused Tricyclic Compound itself is administered to the patient, and not a salt thereof.

Combination Therapy

The Fused Tricyclic Compounds may be used in combination with one or more additional therapeutic agents in the treatment, prevention, suppression or amelioration of diseases or conditions for which the Fused Tricyclic Compounds or the other agents may have utility, where the combination of the drugs together are safer or more effective than either agent alone. Such additional therapeutic agent(s) may be administered, by a route and in an amount commonly used therefore, contemporaneously or sequentially with a Fused Tricyclic Compound.

The other therapeutic agents known to be useful in the treatment of Parkinson's disease that can be administered in combination with the Fused Tricyclic Compounds include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

When a Fused Tricyclic Compound is used contemporaneously with one or more additional therapeutic agents, a pharmaceutical composition in unit dosage form containing such additional therapeutic agents and the Fused Tricyclic Compound can be used. However, the combination therapy may also include therapies in which the Fused Tricyclic Compound and one or more additional therapeutic agents are administered on different overlapping schedules. In some embodiments, when used in combination with one or more additional therapeutic agents, the Fused Tricyclic Compounds and the additional therapeutic agents may be used in lower doses than when each is used alone.

Accordingly, as discussed further below, the pharmaceutical compositions of the present invention include those that contain one or more additional therapeutic agents, in addition to a Fused Tricyclic Compound.

When administering an additional therapeutic agent in combination with a Fused Tricyclic Compound, the weight ratio of the Fused Tricyclic Compound to the additional therapeutic agent may be varied and will depend upon the effective dose of each agent. Generally, a therapeutically effective dose of each will be used. Thus, for example, when a Fused Tricyclic Compound is combined with an additional therapeutic agent, the weight ratio of the Fused Tricyclic Compound to the additional agent will generally range from about 1000:1 to about 1:1000, preferably about 200:1 to about 1:200. Combinations of a Fused Tricyclic Compound and additional therapeutic agents will generally also be within the aforementioned range, but in each case, an effective dose of each active ingredient should be used.

Compositions and Administration

This invention is also directed to pharmaceutical compositions which comprise at least one Fused Tricyclic Compound, or a pharmaceutically acceptable salt of said compound and at least one pharmaceutically acceptable carrier.

When administered to a patient, the Fused Tricyclic Compounds can be administered as a component of a composition that comprises a pharmaceutically acceptable carrier or vehicle. The present invention provides pharmaceutical compositions comprising an effective amount of at least one Fused Tricyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Liquid form preparations may include compositions suitable for topical applications, such as are used for dermatological applications.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Fused Tricyclic Compounds of the present invention may also be delivered transdermally. The transdermal compositions can take the form of creams, lotions, aerosols, foams and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., anti-Parkinson's activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Fused Tricyclic Compound is administered orally.

In another embodiment, the Fused Tricyclic Compound is administered intravenously.

In still another embodiment, the Fused Tricyclic Compound is administered sublingually.

In one embodiment, a pharmaceutical preparation comprising at least one Fused Tricyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Compound (s) by weight or volume. In various embodiments, the present compositions can contain, in one embodiment, from about 1% to about 70% or from about 5% to about 60% of the Fused Tricyclic Compound(s) by weight or volume.

The quantity of the Fused Tricyclic Compound in a unit dose of preparation may be varied or adjusted from about 1 mg to about 2500 mg. In various embodiments, the quantity is from about 10 mg to about 1000 mg, 1 mg to about 500 mg, 1 mg to about 100 mg, and 1 mg to about 50 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

For administration to human patients, the amount and frequency of administration of the Fused Tricyclic Compound will be regulated according to the judgment of the attending clinician considering such factors as age, condition and size of the patient as well as severity of the symptoms being treated. Generally, a total daily dosage of the Fused Tricyclic Compound is in the range of from about 0.1 to about 2000 mg per day, although variations will necessarily occur depending on the target of therapy, the patient and the route of administration. In one embodiment, the dosage is from about 1 to about 300 mg/day, administered in a single dose or in 2-4 divided doses. In another embodiment, the dosage is from about 10 to about 1000 mg/day, administered in a single dose or in 2-4 divided doses. In another embodiment, the dosage is from about 100 to about 1000 mg/day, administered in a single dose or in 2-4 divided doses. In still another embodiment, the dosage is from about 100 to about 500 mg/day, administered in a single dose or in 2-4 divided doses.

A typical recommended dosage regimen for the Fused Tricyclic Compound is oral administration of from 10 mg to 2000 mg/day preferably 10 to 1000 mg/day, in two to four divided doses to provide relief from central nervous system diseases such as Parkinson's disease or the other disease or conditions listed above.

The compositions of the invention can further comprise one or more additional therapeutic agents, selected from those listed above herein. Accordingly, in one embodiment, the present invention provides compositions comprising: (i) at least one Fused Tricyclic Compound or a pharmaceutically acceptable salt, solvate, ester or prodrug thereof; (ii) one or more additional therapeutic agents that are not a Fused Tricyclic Compound; and (iii) a pharmaceutically acceptable carrier, wherein the amounts in the composition are together effective to treat a central nervous disease or disorder.

When the Fused Tricyclic Compounds are used in combination with dopaminergic agents, the doses and dosage regimen of the dopaminergic agents will be determined by the attending clinician in view of the approved doses and dosage regimen in the package insert, taking into consideration the age, sex and condition of the patient and the severity of the disease. It is expected that when the combination of a Fused Tricyclic Compound and a dopaminergic agent is administered, lower doses of the components will be effective compared to the doses of the components administered as monotherapy.

Kits

Another aspect of this invention is a kit comprising a therapeutically effective amount of at least one Fused Tricyclic Compound, or a pharmaceutically acceptable salt, solvate, ester or prodrug of said compound and a pharmaceutically acceptable carrier, vehicle or diluent.

Yet another aspect of this invention is a kit comprising an amount of at least one Fused Tricyclic Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the at least one Fused Tricyclic Compound and the at least one additional therapeutic agent are provided in the same container. In one embodiment, the at least one Fused Tricyclic Compound and the at least one additional therapeutic agent are provided in separate containers.

Another aspect of this invention is a kit containing the at least one Fused Tricyclic Compound (and any additional therapeutic agents) packaged for retail distribution (i.e., an article of manufacture or a kit). Such articles will be labeled and packaged in a manner to instruct the patient how to use the product. Such instructions will include the condition to be treated, duration of treatment, dosing schedule, etc.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. The following compounds, or a pharmaceutically acceptable salt thereof:

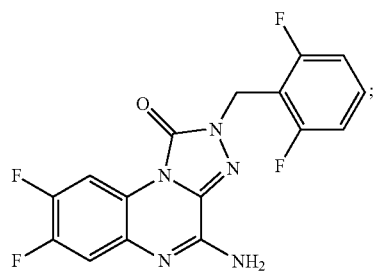

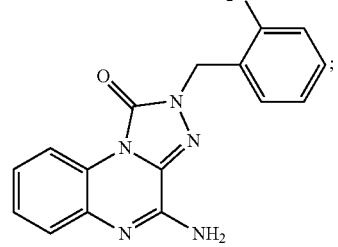

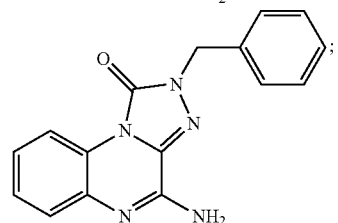

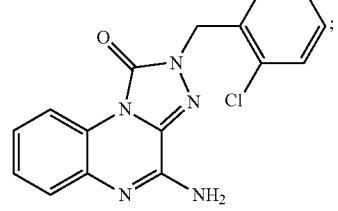

-continued

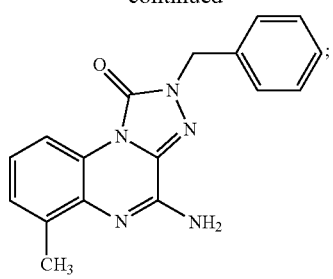

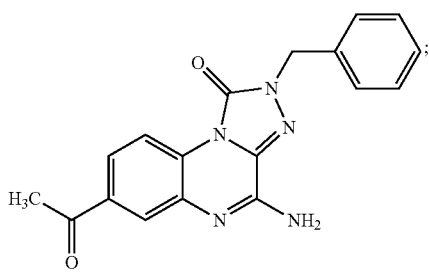

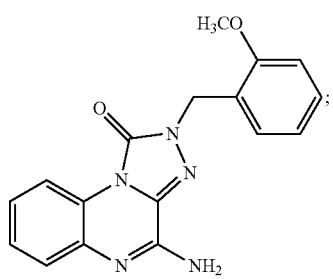

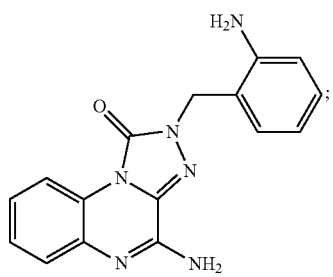

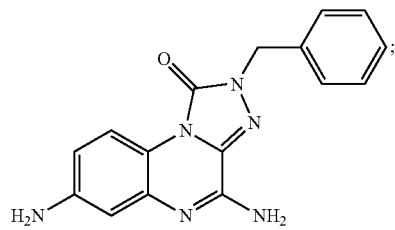

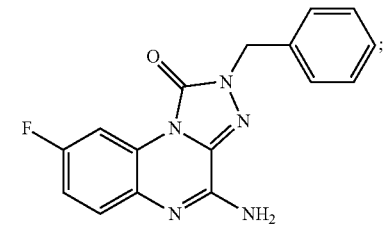

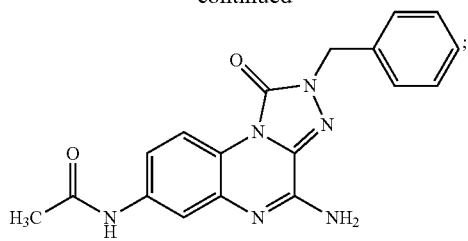
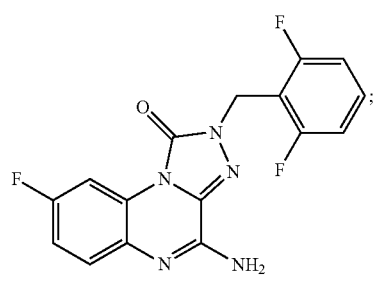
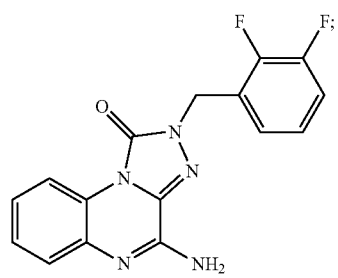
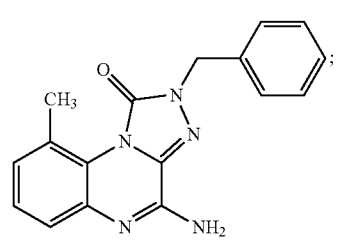
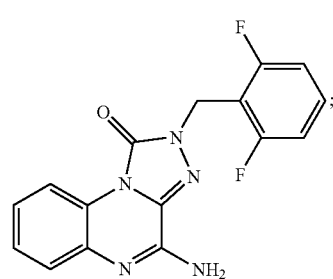
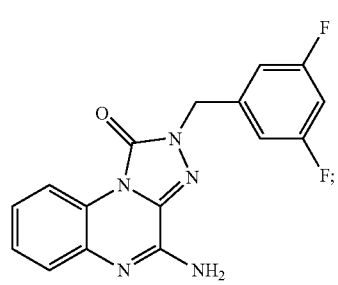
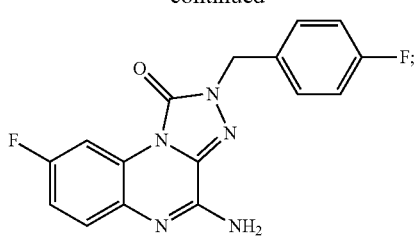
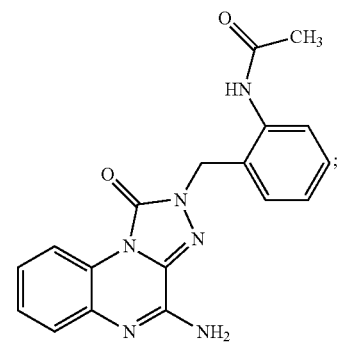
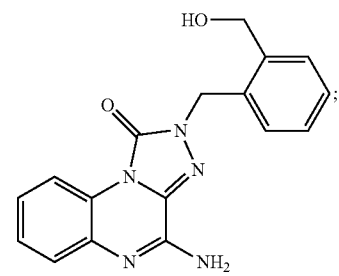
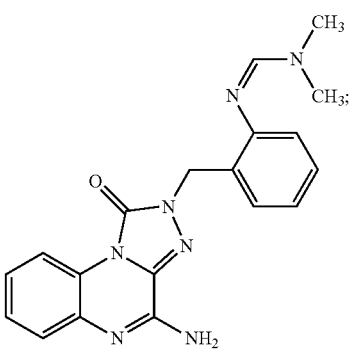
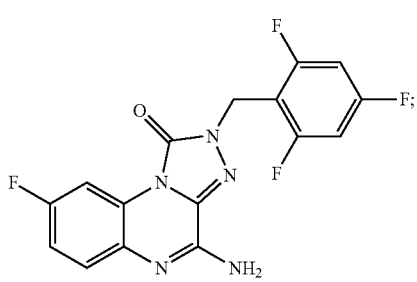
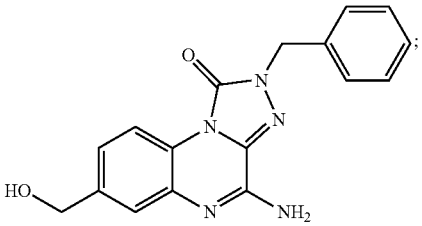

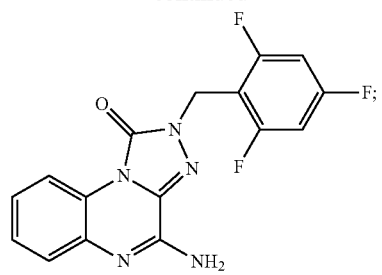
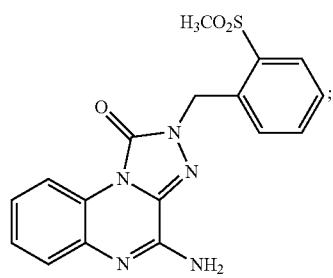
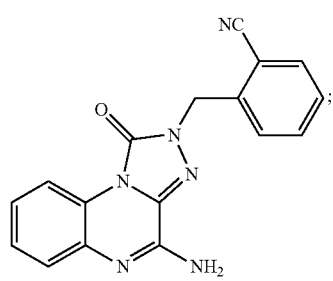
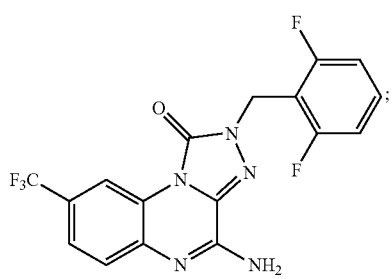
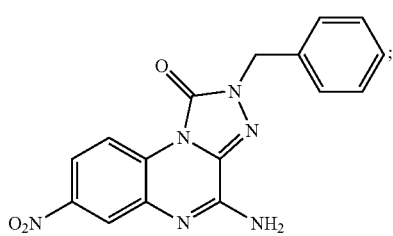
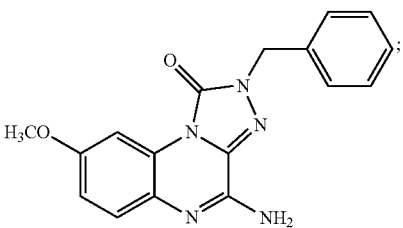
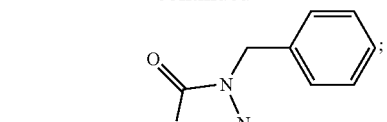
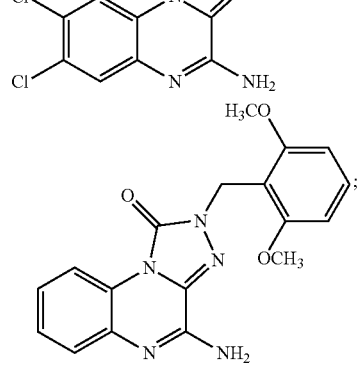
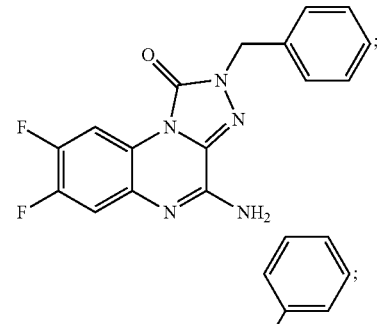
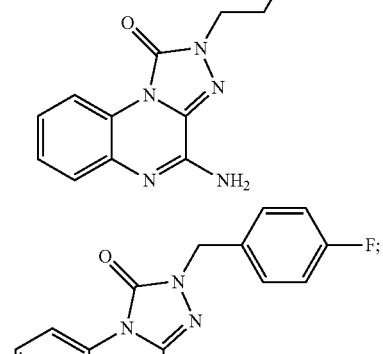
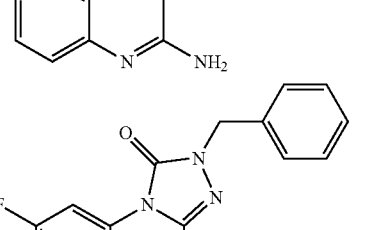
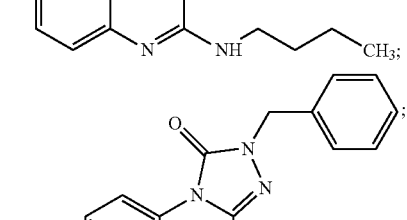
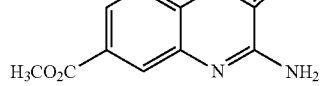

79
-continued
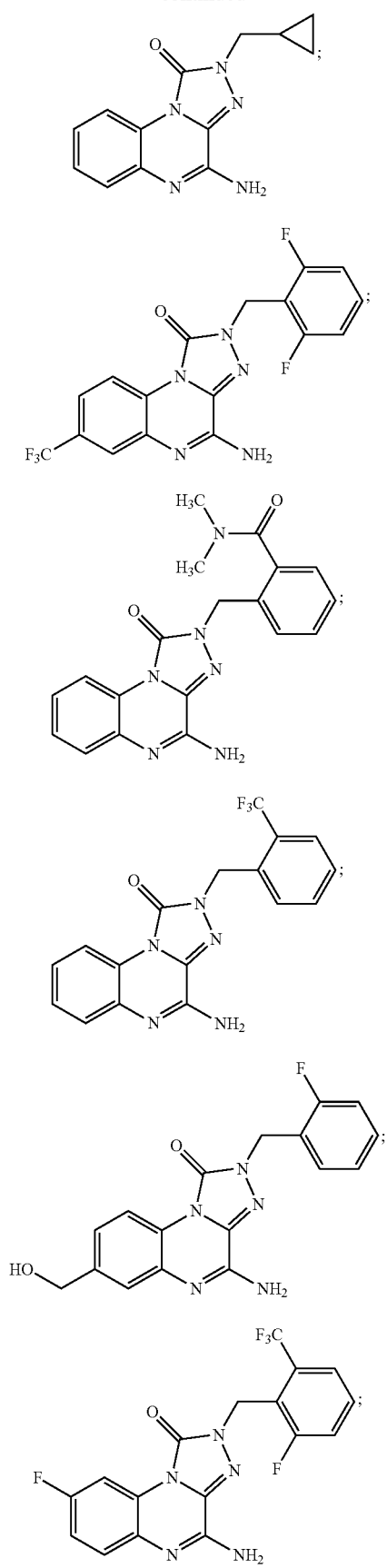
80
-continued
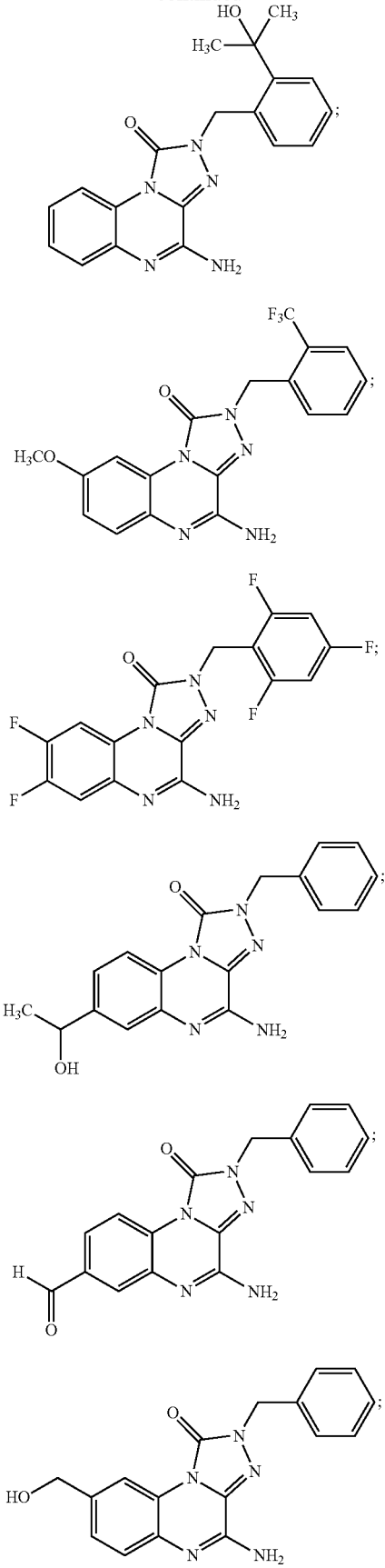

-continued
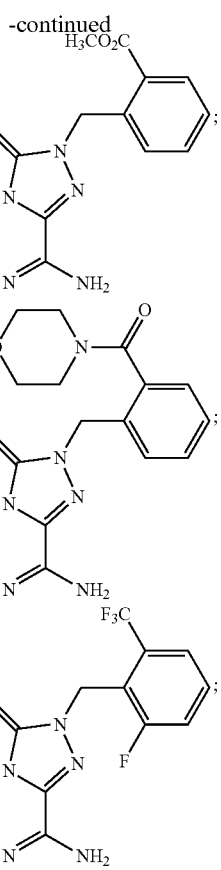
-continued
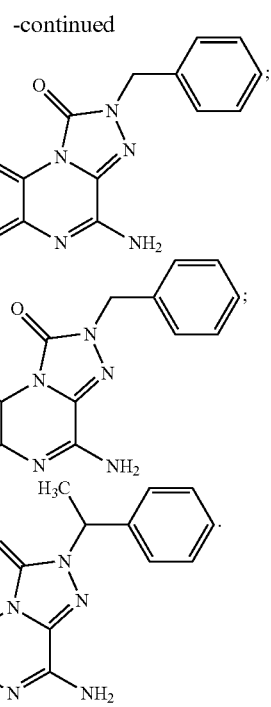
2. A pharmaceutical composition comprising a therapeutically effective amount of a compound of claim 1 or a pharmaceutically acceptable salt thereof and a pharmaceutically acceptable carrier.
* * * * *